United States Patent [19]
Dobak, III et al.

[11] Patent Number: 5,758,505
[45] Date of Patent: Jun. 2, 1998

[54] PRECOOLING SYSTEM FOR JOULE-THOMSON PROBE

[75] Inventors: John D. Dobak, III; Terry L. Brown; Kambiz Ghaerzadeh; Xiaoyu Yu, all of San Diego, Calif.

[73] Assignee: CryoGen, Inc., San Diego, Calif.

[21] Appl. No.: 726,770

[22] Filed: Oct. 7, 1996

Related U.S. Application Data

[63] Continuation-in-part of Ser. No. 698,044, Aug. 15, 1996, which is a continuation-in-part of Ser. No. 542,123, Oct. 12, 1995.

[51] Int. Cl.⁶ .................................................. F25B 19/02
[52] U.S. Cl. .................. 62/6; 62/51.2; 62/293; 606/23
[58] Field of Search .................... 62/51.2, 293, 6; 606/23

[56] References Cited

U.S. PATENT DOCUMENTS

| | | | |
|---|---|---|---|
| 3,272,203 | 9/1966 | Chato | 128/303.1 |
| 3,273,356 | 9/1966 | Hoffman | 62/51.2 |
| 3,298,371 | 1/1967 | Lee | 62/293 |
| 3,398,738 | 8/1968 | Lamb et al. | 128/303.1 |
| 3,401,533 | 9/1968 | Maybury | 62/51.2 |
| 3,431,750 | 3/1969 | Lefranc | 62/51.2 |
| 3,439,680 | 4/1969 | Thomas, Jr. | 128/303.1 |
| 3,477,434 | 11/1969 | Hood, Jr. et al. | 128/303.1 |
| 3,536,075 | 10/1970 | Thomas, Jr. | 128/303.1 |
| 3,662,755 | 5/1972 | Rautenbach et al. | 128/303.1 |

(List continued on next page.)

FOREIGN PATENT DOCUMENTS

| | | | |
|---|---|---|---|
| 2 477 406 | 9/1981 | France . | |
| 1 774 140 | 11/1992 | Russian Federation . | |
| 0 839 516 | 6/1981 | U.S.S.R. . | |
| 1 336 892 | 11/1973 | United Kingdom . | |
| 2 080 117 | 2/1982 | United Kingdom . | |
| WO 95/13025 | 5/1995 | WIPO | A61B 17/36 |

OTHER PUBLICATIONS

Chang, Zhaohua; *Development of a High–Performance Multiprobe Cryosurgical Device*; pp. 383–390; Sep., 1994; Biomedical Instrumentation and Technology, vol. 28.

Coxeter, Ruth; *Developments to Watch—The Deep Freeze for Irregular Heartbeats*; p. 90; Sep. 19, 1994; Business Week.

Friend Daniel G.; *Thermophysical Property Computer Packages from NIST*; pp. 13–18; 1992; ASME HTD vol. 225, Computerized Thermophysical Property Packages.

Gage Andrew A.; *Current Progress in Cryosurgery*; pp. 483–486; Mar. 1988; American College of Cryosurgery, 8th Annual Meeting.

(List continued on next page.)

*Primary Examiner*—Christopher B. Kilner
*Attorney, Agent, or Firm*—Gerald W. Spinks

[57] ABSTRACT

A miniature mixed gas refrigeration system and method of operation are disclosed. An optimum gas mixture is formulated from a group of component fluids, according to calculated thermodynamic properties of a group of candidate fluid mixtures. The gas mixture is pressurized by a compressor to a pressure less than 420 psia, for safety reasons. The compressed gas mixture is passed through a primary heat exchanger, and then through a primary-to-secondary heat exchanger, to precool the gas mixture. The secondary side of the primary/secondary heat exchanger is cooled by a secondary Joule-Thomson refrigeration system. Properly sized flow restrictions in the primary side of the primary/secondary heat exchanger can solidify and trap liquid contaminants that may be in the gas mixture. The gas mixture exiting the primary outlet of the primary/secondary heat exchanger passes to a primary Joule-Thomson expansion element where the high pressure gas is expanded isenthalpically to a lower temperature at least as low as 183K. This low temperature gas cools a heat transfer element mounted in the outer wall of the catheter, to cool an external object. Return gas flows back through the primary heat exchanger to further pre-cool the incoming high pressure gas mixture. A distal primary heat exchanger can be added between the primary/secondary heat exchanger and the primary Joule-Thomson expansion element.

36 Claims, 27 Drawing Sheets

U.S. PATENT DOCUMENTS

| | | | |
|---|---|---|---|
| 3,913,581 | 10/1975 | Ritson et al. | 128/303.1 |
| 4,015,606 | 4/1977 | Mitchiner et al. | 62/293 |
| 4,207,897 | 6/1980 | Lloyd et al. | 128/303.1 |
| 4,377,168 | 3/1983 | Rzasa et al. | 128/303.1 |
| 4,781,033 | 11/1988 | Steyert et al. | 62/51.2 |
| 4,829,785 | 5/1989 | Hersey | 62/51.2 X |
| 4,840,043 | 6/1989 | Sakitani et al. | 62/51.2 |
| 4,875,346 | 10/1989 | Jones et al. | 62/467 |
| 4,951,471 | 8/1990 | Sakitani et al. | 62/51.2 |
| 4,990,412 | 2/1991 | Hersey | 429/8 |
| 5,063,747 | 11/1991 | Jones et al. | 62/461 |
| 5,078,713 | 1/1992 | Varney | 606/23 |
| 5,101,894 | 4/1992 | Hendricks | 62/51.2 |
| 5,139,496 | 8/1992 | Hed | 606/23 |
| 5,147,355 | 9/1992 | Friedman et al. | 606/23 |
| 5,157,938 | 10/1992 | Bard et al. | 62/335 |
| 5,275,595 | 1/1994 | Dobak, III | 606/23 |
| 5,281,212 | 1/1994 | Savage et al. | 606/15 |
| 5,281,213 | 1/1994 | Milder et al. | 606/15 |
| 5,281,215 | 1/1994 | Milder | 606/20 |
| 5,281,217 | 1/1994 | Edwards et al. | 606/41 |
| 5,324,286 | 6/1994 | Fowle | 606/23 |
| 5,337,572 | 8/1994 | Longsworth | 62/51.2 |
| 5,365,750 | 11/1994 | Greenthal | 62/51.2 |
| 5,423,807 | 6/1995 | Milder | 606/20 |
| 5,595,065 | 1/1997 | Boiarski et al. | 62/51.2 X |

OTHER PUBLICATIONS

Hill, Dennis; *Throttle Cycle Cooler Vibration Characterization*; 5 pages; date and place of publication unknown.

Hubbell, Richard H.; *New Heat Transfer and Friction Factor Design Data for Perforated Plate Heat Exchangers*; pp. 383–390; 1988; Advanced Cryogenic Engineering, vol. 33.

Jichuan, Hu; *Heat Transfer Characteristics of a Perforated Plate: Part II—Heat Transfer Coefficients for the Separate Working Surfaces*; pp. 318–322; Sep., 1990; Cryogenics, vol. 30.

Jones, Jack A.; *Cryogenic Mixed Fluid Application Study and Computer Code Development, Final Report*; pp. i–18; date and place of publication unknown.

Khatri, Ajay; *A Throttle Cycle Cryocooler Operating with Mixed Gas Refrigerants in 70K to 120K Temperature Range*; 5 pages; date and place of publication unknown.

Khatri, Ajay; *A Throttle Cycle Refrigerator Operating Below 77K*; 8 pages; date and place of publication unknown.

Little, W. A.; *Advances in Joule–Thomson Cooling*; pp. 1–10; date and place of publication unknown.

Venkatarathnam, G.; *Matrix Heat Exchangers and Their Application in Cryogenic Systems*; pp. 907–918; Nov. 1990; Cryogenics, vol. 30.

First list of abstracts related to perforated plate heat exchangers, compiled for the applicant through a computer date base search; list not published.

Second list of abstracts related to perforated plate heat exchangers, compiled for the applicant through a computer data base search; list not published.

Venkatarathnam, G.; *Heat Transfer and Flow Friction Correlations in Perforated Plate Matrix Heat Exchangers*; pp. 313–317; Sep., 1990; Cryogenics, vol. 30.

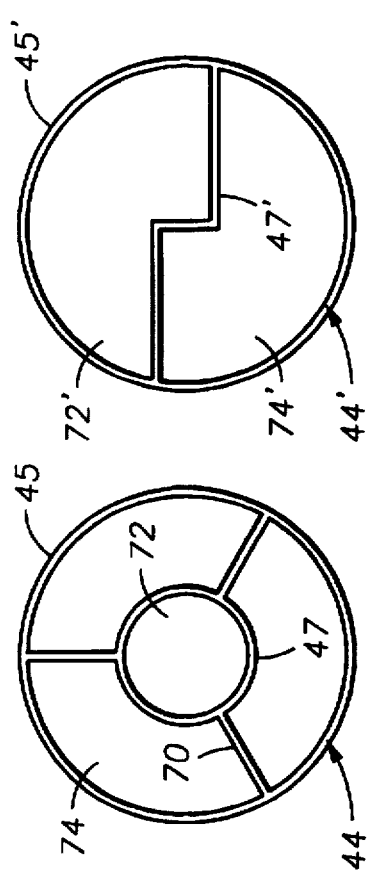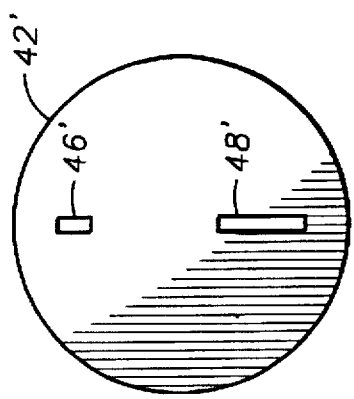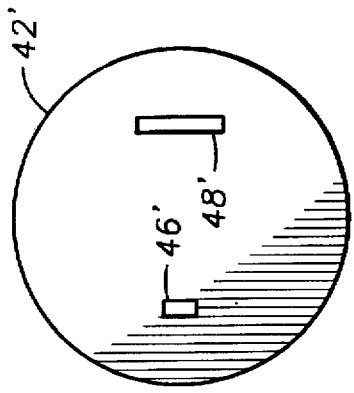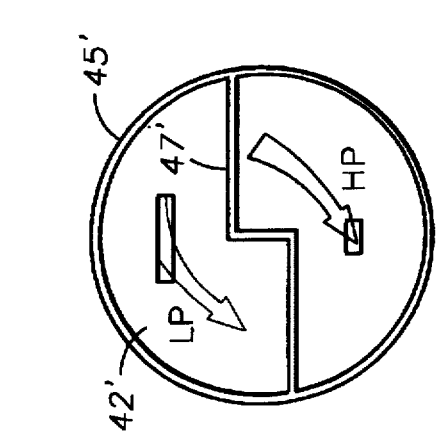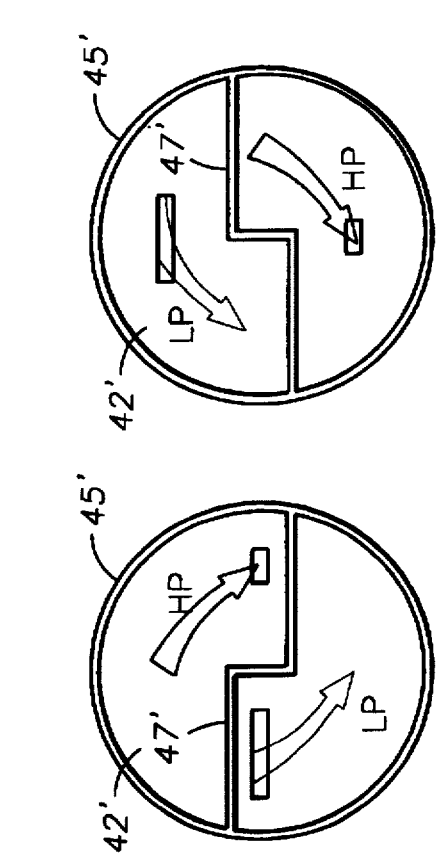

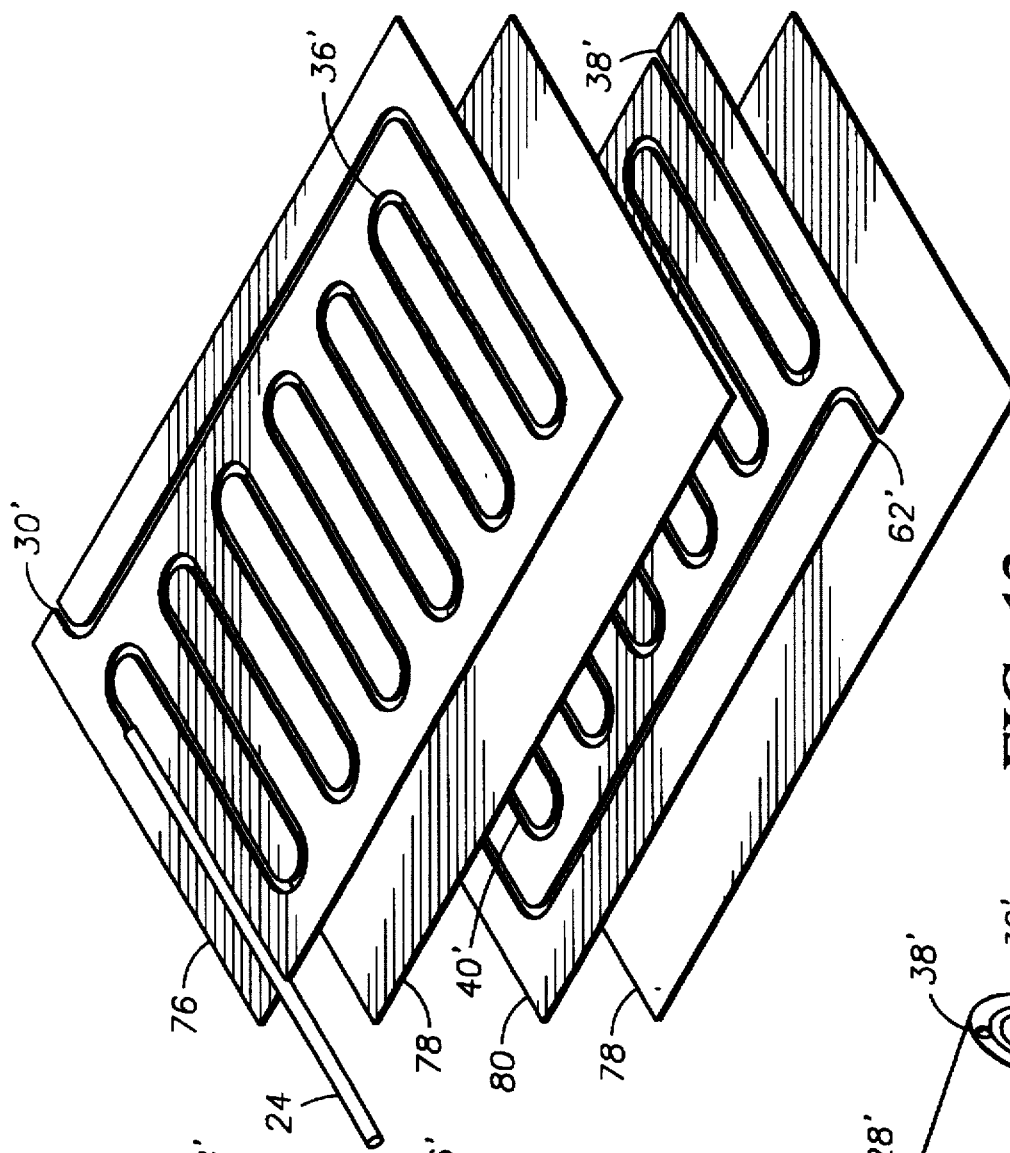
FIG. 12
FIG. 11
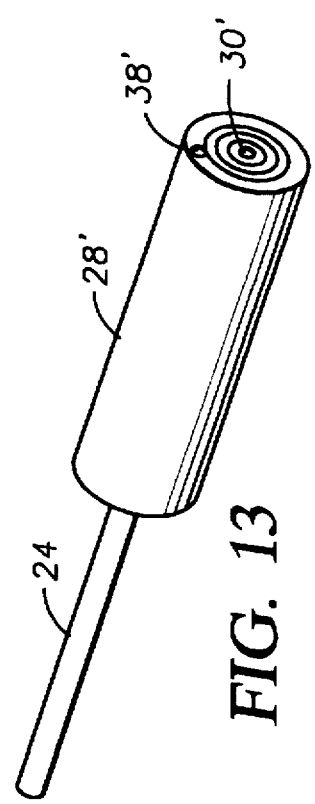
FIG. 13

PRECOOLING SYSTEM FOR JOULE-THOMSON PROBE

CROSS REFERENCE TO RELATED APPLICATIONS

This application is a continuation-in-part of prior copending U.S. patent application Ser. No. 08/698,044, filed Aug. 15 1996, for Mixed Gas Refrigeration Method, which was a continuation-in-part of U.S. patent application Ser. No. 08/542,123, filed Oct. 12 1995, for Miniature Mixed Gas Refrigeration System.

FEDERALLY SPONSORED RESEARCH OR DEVELOPMENT

The U.S. Government has a paid up license in this invention and the right to have this invention practiced on behalf of the Government, as provided for by the terms of Contract No. CRADA: CN-1090, awarded by the National Institute of Standards and Technology.

BACKGROUND OF THE INVENTION

This invention is in the field of cooling miniature objects or very small portions of objects to very low temperatures. The objects to be cooled may include biological matter, electronic components, and others.

In many different fields of endeavor, it is desirable to be able to selectively cool a very small or even microscopic object to a very low temperature without affecting the temperature of surrounding objects. This is true in the field of electronics, where it may be desirable to apply cooling to a miniature component on a circuit board without substantially cooling adjacent components. It is also true in the field of medicine, where it may be desirable to be able to cool miniature discrete portions of biological tissue to very low temperatures in the performance of cryosurgery, without substantially cooling adjacent tissues of the organ. In the interest of simplicity, this specification will address the fulfillment of this need in the field of medicine, but it should be understood that application of the present invention in other fields, such as electronics, is also contemplated within the scope of the present invention.

Cryosurgery has become an important procedure in medical, dental, and veterinary fields. Particular success has been experienced in the specialties of gynecology and dermatology. Other specialties, such as neurosurgery and urology, could also benefit from the implementation of cryosurgical techniques, but this has only occurred in a limited way. Unfortunately, currently known cryosurgical instruments have several limitations which make their use difficult or impossible in some such fields. Specifically, known systems are not optimally designed to have sufficient precision and flexibility to allow their widespread use endoscopically and percutaneously.

In the performance of cryosurgery, it is typical to use a cryosurgical application system designed to suitably freeze the target tissue, thereby destroying diseased or degenerated cells in the tissue. The abnormal cells to be destroyed are often surrounded by healthy tissue which must be left uninjured. The particular probe or other applicator used in a given application is therefore designed with the optimum shape and size for the application, to achieve this selective freezing of tissue. Where a probe is used, the remainder of the refrigeration system must be designed to provide adequate cooling, which involves lowering the operative portion of the probe to a desired temperature, and having sufficient power or capacity to maintain the desired temperature for a given heat load. The entire system must be designed to place the operative portion of the probe at the location of the tissue to be frozen, without having any undesirable effect on other organs or systems.

Currently known cryosurgical systems typically use liquid nitrogen or nitrous oxide as coolant fluids. Liquid nitrogen is usually either sprayed onto the tissue to be destroyed, or it is circulated to cool a probe which is applied to the tissue. Liquid nitrogen has an extremely low temperature of approximately 77K, and a high cooling power, making it very desirable for this purpose. However, liquid nitrogen typically evaporates and escapes to the atmosphere during use, requiring the continual replacement of storage tanks. Further, since the liquid is so cold, the probes and other equipment used for its application require vacuum jackets or other types of insulation. This makes the probes relatively complex, bulky, and rigid, and therefore unsuitable for endoscopic or intravascular use. The need for relatively bulky supply hoses and the progressive cooling of all the related components make the liquid nitrogen instruments less than comfortable for the physician, as well, and they can cause undesired tissue damage.

A nitrous oxide system typically achieves cooling by pressurizing the gas and then expanding it through a Joule-Thomson expansion element, such as a valve, orifice, or other type of flow constriction, at the end of a probe tip. Any such device will be referred to hereinafter simply as a Joule-Thomson "expansion element". The typical nitrous oxide system pressurizes the gas to 700 to 800 psia., to reach practical temperatures of no lower than about 190K to 210K. Nitrous oxide systems are not able to approach the temperature and power achieved by the nitrogen systems. The maximum temperature drop that can be achieved in a nitrous oxide system is to 184K, which is the boiling point of nitrous oxide. The nitrous oxide system does have some advantages, in that the inlet high pressure gas is essentially at room temperature until it reaches the Joule-Thomson element at the probe tip. This eliminates the need for insulation of the system, facilitating miniaturization and flexibility to some extent. However, because of the relatively warm temperatures and low power, tissue destruction and other applications are limited. For many such applications, temperatures below 184K are desirable. Further, the nitrous oxide must typically be vented to atmosphere after passing through the system, since affordable compressors suitable for achieving the high pressures required are not reliable and readily commercially available.

In most Joule-Thomson systems, single non-ideal gasses are pressurized and then expanded through a throttling component or expansion element, to produce isenthalpic cooling. The characteristics of the gas used, such as boiling point, inversion temperature, critical temperature, and critical pressure determine the starting pressure needed to reach a desired cooling temperature. Joule-Thomson systems typically use a heat exchanger to cool the incoming high pressure gas with the outgoing expanded gas, to achieve a higher drop in temperature upon expansion and greater cooling power. For a given Joule-Thomson system, the desired cooling dictates the required heat exchanger capacity. Finned tube heat exchangers have been used, but these are necessarily bulky to achieve the required cooling, preventing their use in micro-miniature systems such as catheter delivered instruments. Smaller heat exchangers have also been known, constructed of photo-etched glass plates. These heat exchange systems are still in the range of several centimeters square in size, making them still too bulky for true micro-miniature use, such as in endoscopes, catheters, and other systems. Further, these heat exchangers are planar and difficult to incorporate into tubular structures such as catheters or endoscopes. In many of these medical applications, the dimensions of the components must be less than approximately 3 mm. in width to allow incorporation into a catheter or endoscope, and preferably less than 15 mm. in length to allow sufficient flexibility.

Heat exchanger requirements can be reduced somewhat by pre-cooling the gases prior to the probe tip heat exchanger. This can be done by incorporating a Peltier device in the flow path prior to the probe tip heat exchanger. Gas flowing through a heat exchanger on the surface of the cold side of the Peltier device would be cooled prior to reaching the probe tip heat exchanger. Alternatively, the inlet high pressure stream could be split so that a portion of the stream could be diverted and expanded to cool the remaining portion of the inlet stream prior to reaching the probe tip heat exchanger.

A dramatic improvement in cooling in Joule-Thomson systems can be realized by using a mixture of gasses rather than a single gas. For example, the addition of hydrocarbons to nitrogen can increase the cooling power and temperature drop for a given inlet pressure. Further, it is possible to reduce the pressure and attain performance comparable to the single gas system at high pressure. Similar to single gas systems, these mixed gas systems have heat exchanger requirements and are limited in their miniaturization potential by the size of the heat exchanger. The improvement in cooling performance realized by mixed gas systems is very desirable for medical and other microminiature systems.

Some mixed gas systems have been designed where high pressure is not a major concern, and where bulky high efficiency heat exchangers can be used, but they are typically used in defense and aerospace applications. The glass plate heat exchangers mentioned above are used in some such systems, and these systems sometimes require pressures of 1200 psia. In many applications, such as laser systems, superconductors, electronics and cryosurgery, pressures above approximately 420 psia. are undesirable for safety reasons, and because the devices exhibit poor longevity, high cost, and poor reliability. Further, endoscopic or percutaneous use prevents implementation of any heat exchanger having a width of greater than about 3 mm. or a length of more than about 15 mm.

Specifically, it would be desirable to develop a long, slender, flexible cryoprobe, such as a transvascular cardiac catheter. Cardiac catheters must be very slender, in the range of less than 5 mm., and they must exhibit considerable flexibility, in order to be inserted from an access point in a remote blood vessel into the heart. A cryosurgical catheter to be used in such an application must also have a relatively low operating pressure for safety reasons. It must have the cooling power to overcome the ambient heat load imposed by the circulating blood, yet it must be able to achieve a sufficiently low temperature to destroy the target tissue. Finally, the cold heat transfer element must be limited to the tip or end region of the catheter, in order to prevent the damaging of tissue other than the target tissue.

It is an object of the present invention to provide a method and apparatus for precooling a primary loop fluid mixture with a secondary loop Joule-Thomson refrigeration cycle and then using the primary loop fluid mixture in a miniature mixed gas refrigeration system which is capable of achieving a cooling temperature of 183K or less, utilizing a high pressure of no greater than 420 psia., with components capable of fitting within a hand held cryoprobe. It is a further object of the present invention to provide a method and apparatus for precooling a primary loop fluid mixture and then using the fluid mixture in a miniature refrigeration system to provide a sufficiently cool high pressure gas mixture for isenthalpic expansion through a Joule-Thomson expansion element, to achieve an expanded gas temperature of at least as low as 183K, to have sufficient cooling power to maintain this temperature when a heat load is applied, and to perform with an inlet high pressure of no greater than 420 psia.

BRIEF SUMMARY OF THE INVENTION

The present invention comprises a method and apparatus for operating a miniature refrigeration system, including a method for selecting an optimum fluid mixture for use as the primary cooling medium and then precooling the primary fluid mixture with a secondary closed loop Joule-Thomson refrigeration cycle to maximize the available cooling power of the fluid mixture.

The cooling power is an important design parameter of a cryosurgical instrument. With greater cooling power, more rapid temperature decreases occur, and lower temperatures can be maintained at the probe tip during freezing. This ultimately leads to greater tissue destruction. The power of a mixed gas J-T cryosurgical device is a function of the enthalpy difference of the gas mixture and the mass flow rate. Pre-cooling certain gas mixtures will increase the enthalpy difference available for cooling power. In addition, pre-cooling will increase the average mass flow rate by making the gas more dense.

Pre-cooling has two other important ramifications. First, it reduces the size of heat exchangers used in the probe. In the miniature environments envisioned for the used of this apparatus, severe size limitations will be placed upon the heat exchangers used, especially the heat exchanger in the cold tip. For instance, a cardiac catheter necessarily is severely limited in diameter by the diameter of the blood vessels through which the catheter must pass. Further, maneuverability requirements dictate that the catheter be somewhat flexible, and the cold tip heat exchanger will probably be somewhat stiff, if not rigid. Therefore, the allowable length of the cold tip heat exchanger is severely limited. Limitation of the size of the cold tip heat exchanger naturally limits the amount of heat which can be transferred in the heat exchanger. This makes use of pre-cooling particularly beneficial. Second, mixed gas J-T cryosurgical devices require fixed size expansion elements, which can become partially or totally blocked by contaminants such as water or oil. This limits flow rate and decreases cooling power. Pre-cooling allows these contaminants to be cold-filtered and removed from circulation prior to reaching the expansion element.

The term "gas mixture" will be used to some extent in the present application, but it should be understood that this term is not intended to be limited to mixtures having no liquid components, in view of the well known fact that most compositions commonly referred to as gases actually have some liquid content at some temperatures and pressures. The primary closed loop refrigeration system has a primary loop compressor for compressing a primary gas mixture to a pressure up to 420 psia. The method and apparatus of the present invention can be used equally well in a rigid hand held cryoprobe, or in a catheter.

The high pressure primary gas mixture from the primary compressor is fed into a high pressure supply tube, such as an inner tube of a coaxial dual lumen tube leading to the handle of a cryoprobe. The dual lumen tube feeds the high pressure gas mixture into the inlet port at the proximal end of a miniature counterflow primary heat exchanger in the handle. The high pressure primary gas mixture passes through a high pressure supply passageway within the primary heat exchanger and exits through a port at the distal end of the primary heat exchanger. The high pressure passageway of the primary heat exchanger is connected to the inlet of a primary high pressure passageway in a primary-to-secondary heat exchanger also located in the handle of the cryoprobe. The high pressure primary gas mixture passes through the high pressure passageway within the primary-to-secondary heat exchanger and exits through a port at the distal end of the primary-to-secondary heat exchanger.

The primary-to-secondary heat exchanger is part of the secondary closed loop Joule-Thomson refrigeration system which has a secondary compressor, and a secondary Joule-Thomson expansion element, in addition to the primary/secondary heat exchanger. The secondary compressor compresses a secondary refrigerant, usually a single component fluid, to a pressure which can be relatively higher than that used in the primary loop. Since the secondary loop does not flow into the probe, a higher pressure can be used safely. Then, the high pressure secondary refrigerant passes through a high pressure secondary passageway in the primary/secondary heat exchanger. The high pressure secondary refrigerant then passes through the secondary Joule-Thomson expansion element, in which the secondary refrigerant isenthalpically expands to a lower pressure and a lower temperature.

The low pressure secondary refrigerant then passes through a low pressure secondary passageway in the primary/secondary heat exchanger and returns to the secondary compressor. The primary/secondary heat exchanger is constructed so as to interpose the secondary low pressure passageway between the primary high pressure passageway and the secondary high pressure passageway. This insures the transfer of heat from both of the high pressure passageways into the low pressure passageway.

The high pressure passageway of the primary-to-secondary heat exchanger can then be connected to the inlet of a high pressure passageway in a microminiature primary heat exchanger located in the probe, near the cold tip. The high pressure primary gas mixture passes through the high pressure passageway within the microminiature primary heat exchanger and exits through a port at the distal end of the heat exchanger. The high pressure passageway is then connected to the inlet of the primary Joule-Thomson expansion element located in the cold tip, in which the gas mixture is isenthalpically expanded to a lower pressure and a temperature at least as low as 183K. The expansion element can have a second stage in which the gas mixture is further expanded isothermally to absorb additional heat from the surroundings. If the first primary heat exchanger and the primary/secondary heat exchanger have sufficient capacity, it may not be necessary to incorporate the microminiature primary heat exchanger into the system, and the high pressure primary gas mixture can pass directly from the high pressure passageway of the primary/secondary heat exchanger to the primary Joule-Thomson expansion element.

The primary gas mixture exiting the primary Joule-Thomson expansion element is exposed to the inner surface of a heat transfer element mounted in the wall of an outer tube which is coaxial with the inner tube. The expanded primary gas mixture cools the heat transfer element to a temperature of at least as low as 183K and then returns through the low pressure return passageway of the microminiature primary heat exchanger in the cold tip, and through the low pressure return passageway of the miniature primary heat exchanger in the probe handle. This cools the primary high pressure gas from its original ambient temperature to a lower temperature. From the low pressure outlet of the miniature primary heat exchanger in the probe handle, the low pressure expanded primary gas mixture flows into the lumen of the outer coaxial tube, outside the inner high pressure tube, to return to the primary compressor.

Both the miniature primary heat exchanger and the primary/secondary heat exchanger are coiled tube heat exchangers. The miniature primary heat exchanger in the probe handle can be a coiled coaxial tube, with the inner lumen being the high pressure passageway and the outer lumen being the low pressure passageway. The secondary passageways of the primary/secondary heat exchanger can be a coiled coaxial tube, with the inner lumen being the high pressure secondary passageway and the outer lumen being the low pressure secondary passageway. Attached to the side of this outer tube, in a parallel arrangement, is a tube which forms the high pressure primary passageway. The high pressure primary tube can have a plurality of inner tubes, which can be nested and placed in contact with the outer tube for improved heat exchange. High pressure primary gas mixture flows in all of the nested tubes and in the interstitial spaces between the nested tubes and the outer tube. The secondary coaxial tube and the primary tube can be formed of metal and soldered together.

The microminiature heat exchanger in the cold tip can be a single coiled tube surrounded by a low pressure return passageway. Alternatively, it can have a laminated construction of several different types. In one example of the laminated type, the microminiature heat exchanger is constructed of a plurality of plates and spacers stacked alternatingly along the axial dimension of the heat exchanger. The plates have a first plurality of holes establishing the high pressure passageway of the heat exchanger, and a second plurality of holes establishing the low pressure passageway of the heat exchanger. The high pressure holes are segregated from the low pressure holes. Spacers with larger openings are stacked between the plates to promote turbulent flow and insure effective heat exchange. The plates and spacers can be fastened together by a process such as diffusion bonding.

The primary and secondary Joule-Thomson expansion elements can be a sintered metal plug made by sintering a plurality of metal beads into a metal cup, to provide the required pressure drop. Alternatively, the expansion element can be a properly sized orifice or some other type of restriction. The two different stages of the sintered plug expansion element, if present, can utilize different sizes of beads, different cross sectional areas, and different packing densities. The heat transfer element can take the optimum shape for matching the object or tissue to be cooled. For example, a metal plug can be installed in the tip of the outer tube or catheter, for applying cooling through the extreme distal tip of the catheter. Alternatively, a relatively narrow metal strip can be mounted in a side wall of the catheter, near the distal tip, for applying cooling to a narrow strip of tissue.

The severe limitation on the size and capacity of the cold tip heat exchanger dictates that the system be optimized by selection of a gas mixture which will have the appropriate thermodynamic properties to perform as well as possible.

The goal of this selection process is to maximize the cooling power of the combination of the pre-cooling heat exchangers, the cold tip heat exchanger, and the primary Joule-Thomson expansion element. For a given gas mixture operating between selected high and low pressures and between selected high and low temperatures, there is a limit to the amount of heat which can be transferred, even in a perfect heat exchanger. The best use of the apparatus of the present invention requires a method for selecting, from among a group of gas mixture candidates, a mixture which will maximize the performance ratio between the cooling power of the Joule-Thomson expansion element and the heat transfer capacity of a perfect heat exchanger.

The method involves first compiling a list of component fluids, which will be combined in various mixtures to arrive at an optimum mixture. It is necessary for each fluid mixture to have a triple point below the lowest temperature to be encountered, to ensure that the fluid mixture can not possibly freeze in the apparatus. Various methods could be employed to insure that each fluid mixture possesses this quality. One method is to insure that each of the component fluids has a triple point below the lowest temperature to be encountered. This would ensure that any mixture of those fluids would meet this criterion. It is common, however, for a fluid mixture to have a triple point below the triple points of several of its components. Therefore, it would be feasible to use several component fluids having triple points above the lowest temperature to be encountered, as long as the triple point of each fluid mixture is computed to be below the lowest temperature to be encountered.

It is also necessary for the fluid mixture to possess a positive Joule-Thomson coefficient, to ensure that a drop in pressure is accompanied by a drop in temperature. As with the triple point criterion, this can be accomplished by ensuring that each component fluid has a positive Joule-Thomson coefficient. However, it is also possible for a fluid mixture to have a positive Joule-Thomson coefficient, even though several of its component fluids have negative coefficients. Therefore, it would be feasible to use several component fluids having negative coefficients, as long as the coefficient of each fluid mixture is computed to be a positive value.

For each of the component fluids in this list, the molar enthalpy is known at a plurality of data points over a selected range of temperatures and a selected range of pressures, with these ranges including the temperatures and pressures at which the fluid mixture will be pumped through the apparatus. Then, various mixtures of the fluids are selected, with each mixture having up to a selected maximum number of component fluids. Based upon the known thermodynamic properties of the component fluids, the molar enthalpy of each fluid mixture is then calculated at a plurality of data points over the selected range of temperatures and the selected range of pressures.

For each fluid mixture, a series of calculations are then performed. It can be assumed that the pressure drop through the heat exchanger, on either the high pressure side or the low pressure side, is negligible. Alternatively, a starting pressure can be chosen which takes into account the anticipated pressure drop in the heat exchanger. For the low pressure in the selected pressure range, the molar enthalpy of the fluid mixture at the low temperature in the selected temperature range is subtracted from the molar enthalpy at the high temperature in the range, yielding a low pressure enthalpy difference between the fluid mixture states at the two temperatures. Similarly, for the high pressure in the selected pressure range, the molar enthalpy at the low temperature is subtracted from the molar enthalpy at the high temperature, yielding a high pressure enthalpy difference between the fluid mixture states at the two temperatures. The lesser of these two enthalpy differences is the maximum molar enthalpy difference which could be achieved in a perfect counterflow heat exchanger operating with the selected fluid mixture over the selected temperature range and pressure range. The maximum possible heat transfer capacity of such a heat exchanger with the selected fluid mixture is the product of the molar flow rate of the fluid mixture and this molar enthalpy difference.

Then, for each selected fluid mixture, at a plurality of selected temperatures over the selected temperature range, the molar enthalpy of the fluid mixture at the high pressure in the selected pressure range is subtracted from the molar enthalpy at the low pressure in the range, yielding a molar enthalpy difference between the fluid mixture states at the two pressures, for each of the plurality of temperatures. The plurality of temperatures at which this calculation is performed are selected at uniform intervals over the selected temperature range. As an example, if the selected temperature range is from 120K to 270K, the intervals between the selected plurality of temperatures might be set at five degree increments, for a total of 30 intervals, and 31 selected temperatures. This calculation is then performed at each of the 31 temperatures. The higher the number of selected temperatures used, the greater will be the usefulness of the information calculated. The molar enthalpy difference calculated at each of these selected temperatures is the enthalpy increase which would occur during expansion of the selected fluid mixture from the high pressure to the low pressure, if the temperature were to remain constant.

In Joule-Thomson expansion, there is very little or no opportunity for heat transfer to or from the fluid as it flows through the expansion element, no change in potential energy of the fluid, no work performed, and very little or no change in kinetic energy of the fluid. Therefore, the enthalpy states of the fluid before and after the expansion are essentially the same. As the pressure sharply decreases, the temperature of the fluid also sharply decreases, maintaining an essentially constant enthalpy. This colder fluid then can be used to cool the surroundings. The maximum possible cooling power available through Joule-Thomson expansion over the selected pressure range, with the selected fluid mixture, is the product of the molar flow rate of the fluid mixture and the lowest molar enthalpy difference calculated at any temperature over the selected temperature range.

Therefore, each fluid mixture in the group exhibits a maximum possible cooling power and a maximum possible heat transfer capacity. In order to optimize the operation of the apparatus of the present invention, a fluid mixture is chosen from among the candidates described above, which will result in the highest performance ratio between the available cooling power and the available heat transfer across a heat exchanger. That is the optimum fluid mixture within the temperature and pressure ranges selected. It can be seen that, if the performance ratio is equal to or greater than unity, meaning that the available cooling power is as great as the available heat transfer, then the maximum cooling possible over the desired temperature and pressure range can be achieved through Joule-Thomson expansion alone, and no heat exchangers are needed. If the highest performance ratio is less than unity, at least one heat exchanger will be required.

The novel features of this invention, as well as the invention itself, will be best understood from the attached drawings, taken along with the following description, in which similar reference characters refer to similar parts, and in which:

BRIEF DESCRIPTION OF THE DRAWINGS

FIG. 6 is an elevation view of a preferred embodiment of a spacer used in the micro-miniature heat exchanger used in the probe shown in FIG. 3;

FIG. 7 is an elevation view of a second embodiment of a spacer used in a second embodiment of the micro-miniature heat exchanger;

FIG. 8 is an elevation view of a first configuration of plate used in the second embodiment of the micro-miniature heat exchanger;

FIG. 9 is an elevation view of a second configuration of plate used in the second embodiment of the micro-miniature heat exchanger, showing the different orientation of high pressure and low pressure ports;

FIG. 10 is a series of elevation views of plates and spacers used in the second embodiment of the micro-miniature heat exchanger, showing the flow of supply and return gas mixtures;

FIG. 11 is a sectional view of the plurality of plates and spacers shown in FIG. 10, showing the flow of supply and return gas mixtures;

FIG. 12 is a perspective view of a third embodiment of the micro-miniature heat exchanger, prior to final shaping;

FIG. 13 is a perspective view of the heat exchanger shown in FIG. 12, after final shaping;

DETAILED DESCRIPTION OF THE INVENTION

Figure 1:
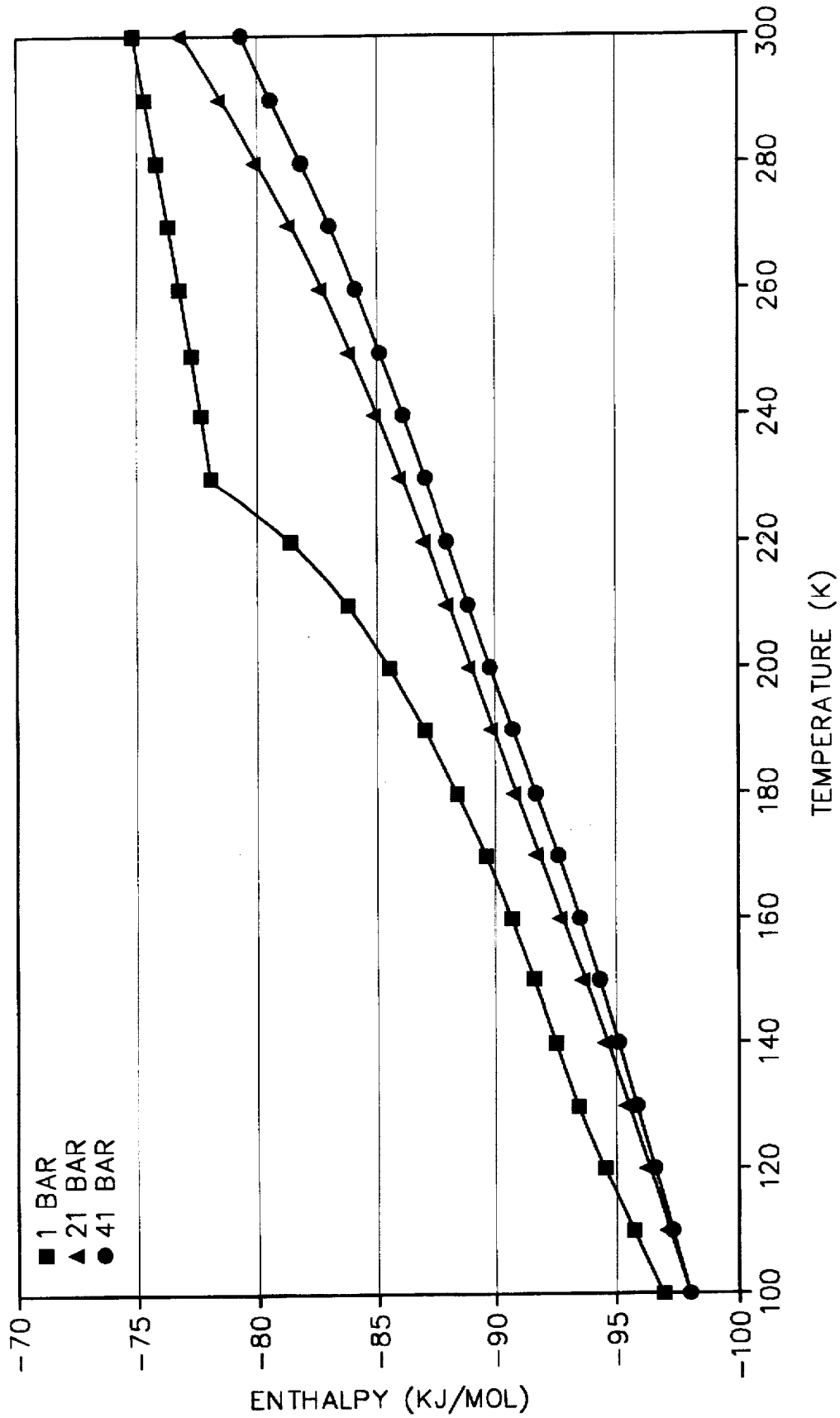
FIG. 1 is a graph of enthalpy vs. temperature for a typical gas mixture used with the present invention.

The present invention lies in the appropriate use of a secondary closed loop Joule-Thomson refrigeration system to precool the primary high pressure gas mixture, before passage of the primary gas mixture through the primary Joule-Thomson expansion element. This is intended to maximize the available cooling power at the tip of the cryosurgical probe.

Pre-cooling the primary fluid mixture prior to feeding it to the micro-miniature heat exchanger in the cold tip is the focus of the present invention. This pre-cooling could be done prior to introducing the primary fluid mixture into the catheter, by the use of a conventional, relatively large, heat exchanger. However, for ease of handling and for maximum efficiency, the present invention focuses on the provision of pre-cooling near the treatment area, such as in the handle of a cryoprobe. This is because minimizing the length of the flow path of precooled fluid maximizes the efficiency of the pre-cooling system.

An important parameter in the design of a cryosurgical device is the cooling power which the refrigeration system can develop. The cooling power determines the rate of cooling in degrees per second, and the temperature which can be maintained at the probe tip during freezing of the tissue. The rate of freezing is important in achieving cell death, since more rapid freezing results in better formation of intracellular ice crystals, resulting in cell lysis. The rate of freezing also determines the length of time required to perform a given procedure on the patient. The quicker the procedure, the less traumatic the procedure is to the patient.

The temperature which can be maintained at the probe cold tip determines the size of the ice ball formed in the surrounding tissue. This, of course, determines the total volume of tissue destroyed at each location, and the speed with which the procedure can be completed. For example, if a first cryoprobe, using a given gas mixture, has 30 watts of cooling power, assume that it can maintain a cold tip temperature of minus 100 degrees C, creating an ice ball of up to 4.5 cm diameter in 15 minutes, in a test gel. Because of the rapid temperature drop, a significant percentage of cell death would occur within a similar size ball of living tissue. By contrast, consider a second cryoprobe, using the same gas mixture, which has only 10 watts of cooling power. The second cryoprobe could only maintain a temperature of minus 50 degrees C, creating an ice ball only 2.5 cm diameter within 15 minutes. Therefore, the aforementioned high percentage of cell death would only occur in a 2.5 cm diameter ball of living tissue, rather than a 4.5 cm diameter ball. Furthermore, if the required size of the ice ball is only 2.5 cm, the first cryoprobe could achieve such an ice ball within 5 minutes, rather than 15 minutes. So, by either standard, the first cryoprobe will achieve a better result, and more quickly, than the lower power second cryoprobe.

In Joule-Thomson cryosurgical devices, high pressure fluid expands across a restriction of some kind, such as a small orifice, or a crimped tube. The sudden drop in pressure results in a corresponding drop in temperature. The cooling power of the device is the product of the mass flow rate of the cryogen and the enthalpy difference at the different pressures and temperatures. The flow rate is a function of orifice size and the temperature and pressure of the cryogen. For a given orifice size, under non-choking conditions, the density of the cryogen is higher at higher pressures and lower temperatures, resulting in a higher mass flow rate. The maximum flow rate is found at the point where the cryogen is a liquid. The enthalpy difference is also a function of the pressure and temperature, with the enthalpy difference between two conditions being higher at higher pressures and lower temperatures. For a given temperature and a given pressure, the maximum enthalpy difference between two conditions occurs at the liquefaction point of the cryogen. One or more pre-cooling heat exchangers can be incorporated into the refrigeration system near the expansion element, to promote cooling or liquefaction of the warm, high pressure cryogen, thereby increasing the power of the system.

Nitrous oxide is the most commonly used cryogen in Joule-Thomson cryosurgical systems. If the high pressure of the system is above 4.5 MPa, nitrous oxide will liquefy upon expansion, without the help of a heat exchanger, and achieve the maximum cooling power. However, nitrous oxide must be operated at this high pressure, and the lowest temperatures available are between minus 50 and minus 70 degrees C, which is relatively warm for some cryosurgical applications. Therefore, the safety and the efficiency of a nitrous oxide system are less than desirable for some applications, such as catheter ablation of heart tissue, and ablation of endometrial tissue.

The fluid mixtures or cryogens discussed in this application operate at lower pressures, and they can achieve lower temperatures, making them both safer and more effective. For example, the mixture of 66% Krypton, 14% R142b, 10% R22, and 10% R23 can reach a temperature of minus 120 degrees C, from a pressure of 2.1 MPa. At a flow rate of 0.6 grams per second, approximately 30 watts of cooling power is achieved. However, this mixture will not liquefy, and reach its maximum cooling power, without the aid of a heat exchanger.

This creates a problem, if this type of mixture is to be used. Since the mixture is in the warm, gaseous state upon startup of the refrigeration system, the early flow rate is very low, and the power is very low. If the heat exchanger used is not very efficient, the initial cool down is very slow at overcoming the low flow rate. Further, the cold tip is typically placed within the patient, and in contact with the target tissue, before commencement of cooldown, placing a significant heat load on the tip. This means that cooldown can be unacceptably slow, and in some cases, it may not occur at all.

Another problem that may occur is the clogging of the expansion element by contaminants. If present, water and oil will liquefy and freeze as the temperature of the cryogen drops. Because of the small size of the orifice or other expansion element, it can be plugged easily. In larger cryosystems, an adjustable orifice can be used, to offset this clogging. However, in the small medical systems, adjustable orifices are too large and unwieldy to be used.

In some mixed gas Joule-Thomson systems, a small degree of pre-cooling can sometimes produce significant increases in cooling power. The selection of a fluid mixture and the use of a pre-cooler must therefore be coordinated.

In order to maximize the performance of mixed gas cryosurgical systems, and to eliminate the problems normally associated with slow cooldown rates and low cooling power, an independent closed loop Joule-Thomson secondary refrigeration system is incorporated into the present invention. The secondary system uses a single refrigerant such as R13b1 to pre-cool the primary gas mixture in the handle of the cryoprobe, prior to flow of the primary gas mixture to the cold tip. The secondary system accomplishes this pre-cooling through a primary/secondary heat exchanger placed as close as possible to the cold tip, to prevent excessive warming of the cooled primary gas mixture before it reaches the cold tip.

This pre-cooling causes the initial flow rate and the cooling power of the system to be higher, making the initial cooldown rate much faster. Selection of the optimal fluid mixture makes the pre-cooling more effective, maximizing the cooling power. With some mixtures, and with pre-cooling, there may be no need for a heat exchanger at the cold tip next to the primary expansion element. A further advantage is that the pre-cooler may act as a cold filter, to eliminate contaminants such as oil and water, which may otherwise clog the expansion element as the system cools down. For this purpose, the a filter can be constructed with openings smaller than the expansion element, but with the total opening area much larger, to avoid creating a significant pressure drop.

The optimization of the present invention also requires the selection of an optimum fluid mixture, since no known single gasses are capable of achieving the necessary cooling power at the required temperatures, given the size limitations and pressure limitations imposed on systems intended for use in the selected applications. Several gas mixtures have been identified for use with the present invention, and it is anticipated that others will be identified as well. Appropriate gas mixtures may take various forms, and they may be either hydrocarbon-based or non-hydrocarbon-based. Some fluid mixtures function significantly better than other mixtures, so it is important to be able to identify and select an optimum mixture from among a group of available mixtures. One mixture currently identified as useful for many applications is 30 percent Methane, 23 percent Nitrogen, 23 percent Isobutane, 19 percent Ethane, and 5 percent Propane. The temperature capability of isenthalpic expansion of such a gas mixture is illustrated by FIG. 1, which shows enthalpy curves for this gas mixture at pressures of 1 bar (14.5 psia.), 21 bar (305 psia.), and 41 bar (595 psia.). Isenthalpic expansion from one of the higher pressures to the lower pressure proceeds horizontally to the left across the graph, accompanied by a drop in temperature. The lowest temperature attainable would be at the point where the curves cross, somewhere below 100K. The lower the temperature of the high pressure gas mixture, the lower the temperature which can be achieved by the isenthalpic expansion through the Joule-Thomson expansion element. It can also be seen from the graph that there is little difference between the temperatures attainable by expanding from 41 bar and expanding from 21 bar. For example, assume that the heat exchanger used is capable of cooling the high pressure gas mixture to a temperature of 210K, just upstream of the expansion element. If a high pressure of 21 bar is used, the isenthalpic expansion will result in a temperature of 180K. If the gas mixture is instead pressurized to 41 bar, the attainable temperature after isenthalpic expansion is still only about 173K. Further, the cooling power, or power, represented by the difference between the high pressure curve and the 1 bar curve at a given temperature is similar, whether the high pressure is 21 bar or 41 bar. Therefore, the added safety achieved by lowering the initial pressure to 21 bar, or approximately 300 psia, results in only a minor loss of performance. Obviously, for a given gas mixture, the more efficient the heat exchange system, the lower the probe temperature that can ultimately be obtained, and the greater will be the cooling power.

Figure 2:
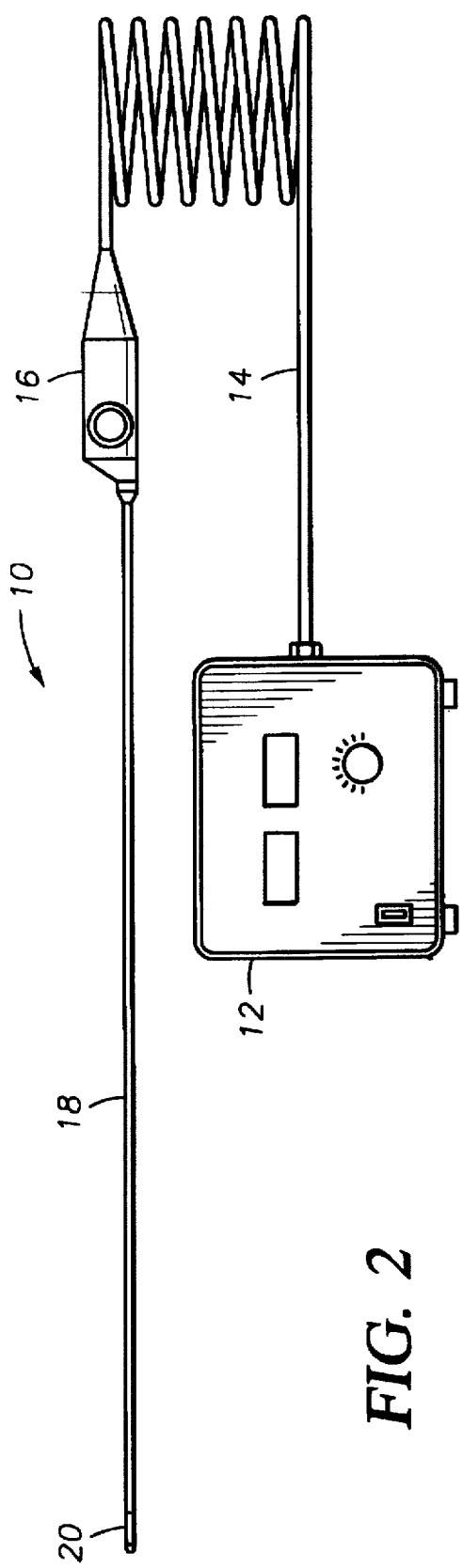
FIG. 2 is a perspective view of one embodiment of the primary portion of the miniature refrigeration system.

FIG. 2 shows the primary loop portion of a refrigeration system 10 according to the present invention, for a cryosurgical application. The primary portion of the system 10 consists of a commercially available single stage compressor 12, a flexible dual lumen hose 14 connected to the inlet and outlet of the compressor 12, a steering handle 16, and a cryosurgical probe 18. The compressor 12 can be any of several compressors available, often using an aftercooler, an oil separator, and an adsorption filter. Alternatively, an oil free compressor could also be utilized. The hose 14 can be any flexible dual lumen hose suitable for the pressures and chemical exposures involved, for the gas mixture used. The handle 16 can have a control expansion element installed, for the physician to use in throttling the flow rate of the gas mixture. Alternatively, the flow could be controlled via a foot switch that regulates flow at the compressor. The probe 18 is a coaxial catheter having an inner tube for conducting the high pressure gas mixture from the outlet of the compressor 12 and for returning the expanded low pressure gas to the inlet of the compressor 12. The probe 18 has a distal end portion or region 20 in which the heat exchanger, expansion element, and heat transfer element are located. The probe 18 is of suitable diameter, length, and flexibility to be inserted to the object to be cooled, such as through the vascular system of a patient into the heart.

Figure 3:
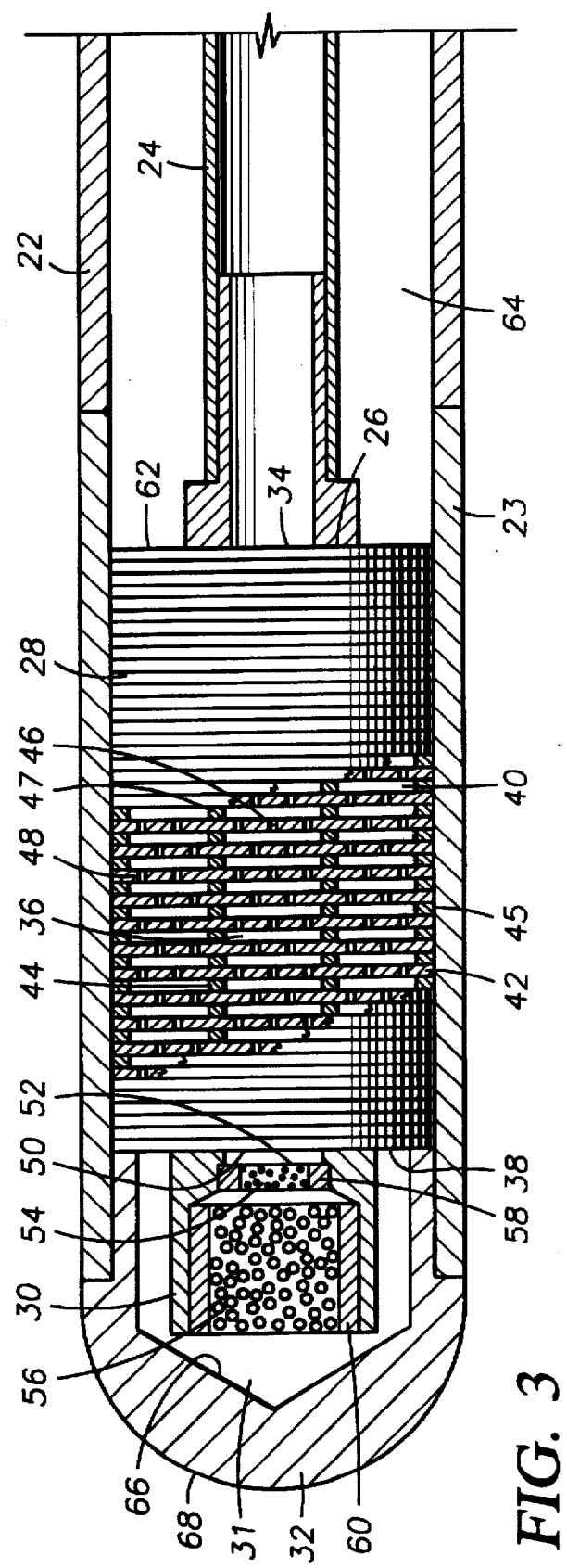
FIG. 3 is a partial section view of the distal end portion of the cryosurgical probe portion of the refrigeration system shown in FIG. 2.

FIG. 3 shows a partial section view of the distal end portion 20 of the coaxial catheter 18. The catheter 18 consists of an outer tube 22 and an inner tube 24. The outer tube 22 can be continuous to the end of the catheter 18, or it can have an extension 23, which should be considered for all practical purposes an integral part of the outer tube 22. The outer tube 22 is made according to known methods from a wire-braided polymer, such as a polyamide-ether copolymer. The inner tube 24 is made from a wire-braided polyimide having a pressure capability sufficient for the maximum high pressure anticipated for the particular application. The inner tube 24 is connected by means of an inlet fitting 26 to the proximal end of a micro-miniature heat exchanger 28. Mounted to the distal end of the heat exchanger 28 is a primary Joule-Thomson expansion element 30. The distal end of the primary expansion element 30 is exposed to a cavity 31 at the distal end of the outer tube 22 or extension 23, closed by a heat transfer element 32. The expanded gas mixture cools the inner surface 66 of the heat transfer element 32, thereby cooling the outer surface 68. The outer surface 68 is placed against the object to be cooled by the physician.

More specifically, the distal end of the inner high pressure tube 24 is connected by means of the inlet fitting 26 to the high pressure inlet port 34 at the proximal end of the heat exchanger 28. This high pressure inlet port 34 leads to a high pressure supply passageway 36 through the heat exchanger, shown as the central axial portion of the heat exchanger 28 in this embodiment. The heat exchanger 28 also has a low pressure inlet port 38 at its distal end exposed to the cavity 31. This low pressure inlet port 38 leads to a low pressure return passageway 40, shown as the outer annular portion of the heat exchanger, surrounding the high pressure passageway 36. The low pressure, low temperature gas mixture flowing through the low pressure passageway pre-cools the high pressure, higher temperature gas mixture flowing through the high pressure passageway. The heat exchanger 28 is constructed of alternately stacked copper plates 42 and stainless steel spacers 44, diffusion bonded together. Other methods of attachment could be used. The heat exchanger 28 is shown, for the sake of simplicity in this figure, as having an outer skin over the plates 42 and spacers 44, but in actuality, the skin is optimally provided by an outer ring 45 on each spacer 44 being bonded to the extreme outer annular portion of each plate 42, as will be made more clear below. The central portion of each plate 42 has a plurality of holes 46 therethrough, which along with central openings in the spacers 44 establish the high pressure passageway 36 longitudinally through the heat exchanger 28 in the distal direction. Similarly, the outer portion of each plate 42 has a plurality of holes 48 therethrough, which along with outer openings in the spacers 44 establish the low pressure passageway 40 longitudinally through the heat exchanger 28 in the proximal direction. The high pressure passageway 36 is separated from the low pressure passageway 40 by an inner ring 47 on each spacer 44.

High pressure gas mixture passing through the heat exchanger 28 exits the high pressure passageway at a high pressure outlet port 50 at the central distal portion of the heat exchanger to enter the inlet 52 of the primary Joule-Thomson isenthalpic expansion element 30. This primary expansion element 30 has a first stage 54 of a first diameter, in which isenthalpic expansion to a second larger diameter takes place, lowering the temperature of the gas mixture to the design temperature. The gas mixture then passes through the second stage 56 in which isothermal expansion takes place, leaving the gas mixture still at the desired temperature, but absorbing heat from the surrounding structure in the process. The first stage 54 is constructed by filling a metal cylinder 58 with a selected size of metal beads, at a selected packing density, to achieve the desired rate of expansion of the gas. The beads are sintered in place in the cylinder 58. Similarly, the second stage 56 is constructed by filling a second metal cylinder 60 with a selected size of metal beads, at a selected packing density, to achieve the desired rate of expansion of the gas. Typically, the beads in the second stage 56 will have a larger surface area to enhance heat transfer.

The expanded primary gas mixture which passes through the heat exchanger 28 in the proximal direction exits the annular low pressure passageway 40 at a low pressure outlet port 62 at the proximal end of the heat exchanger 28. This expanded gas mixture enters the inner lumen 64 of the outer tube 22, surrounding the inner tube 24, to be returned to the primary compressor 12.

Figure 5:
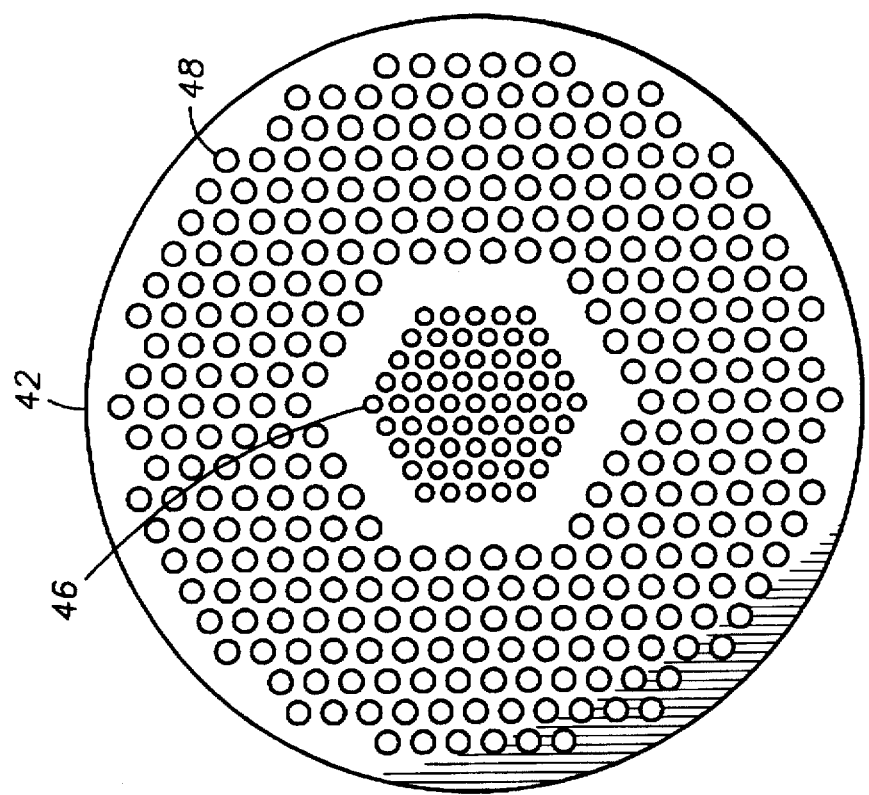
FIG. 5 is an elevation view of a second configuration of heat exchanger plate, showing a different angular orientation of holes from the orientation shown in FIG. 4.
Figure 4:
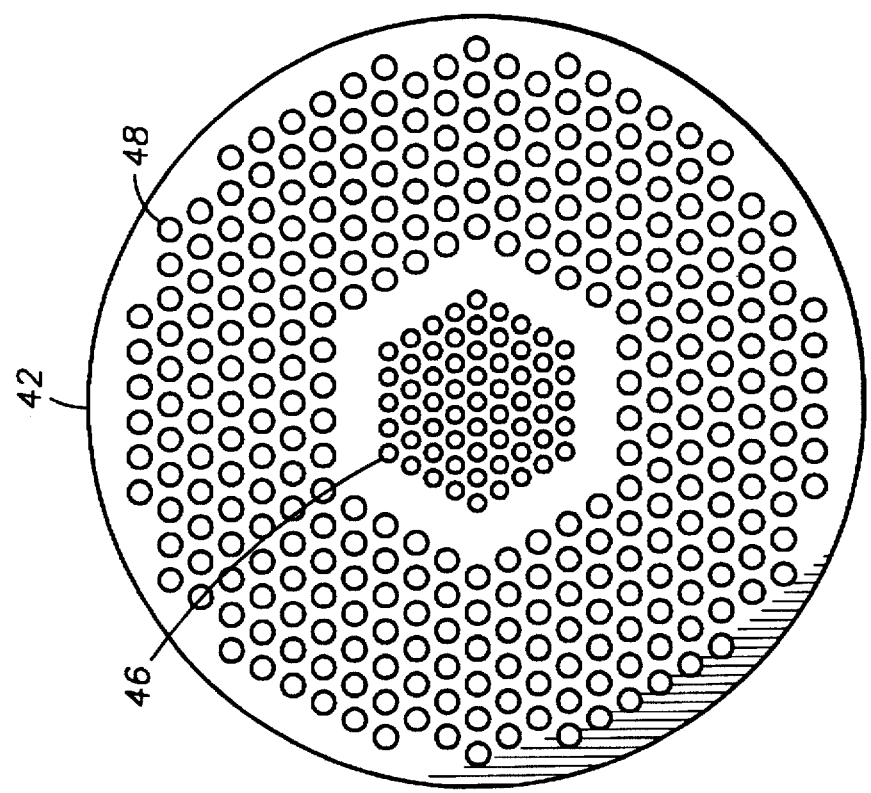
FIG. 4 is an elevation view of a preferred embodiment of one configuration of heat exchanger plate used in the micro-miniature heat exchanger utilized in the cryosurgical probe shown in FIG. 3.

FIGS. 4 and 5 more clearly illustrate the structure of the plates 42 and their angular orientation within the heat exchanger 28. Each plate 42 has a first plurality of high pressure holes 46 through its central portion, and a second plurality of low pressure holes 48 through its outer annular portion. Typically, the diameter and spacing of the inner holes 46 are smaller than the diameter and spacing of the outer holes 48. Selection of hole diameter and spacing for the two different passageways is designed for an optimization of minimum pressure drop and maximum heat transfer rate at the two different pressures, according to well known design principles. FIGS. 4 and 5 are also intended to show the relative angular orientation between adjacent plates 42. It can be seen that the two figures actually depict the same plate configuration, with the plate 42 in FIG. 5 simply being rotated relative to the plate 42 in FIG. 4. The hole pattern used in the plate 42 can be varied, with the objective being to maximize the heat exchange contact between the gas mixture and the plate 42. Gas does not flow from the high pressure portion of the plate to the low pressure portion, being prevented by contact between the plate 42 and the inner ring 47 of the interdisposed spacer 44, as shown earlier in FIG. 3. The relative angular orientation between adjacent plates 42 can also be varied according to the chosen hole pattern, with the objective being to maximize turbulence of the gas mixture, to promote heat transfer. It can be clearly seen from FIGS. 3, 4, and 5 that gas flowing through the heat exchanger 28 in either of the passageways 36, 40 follows a somewhat tortuous path, with a substantial portion of the flow path being involved in movement transverse to the axis of the heat exchanger 28. In the embodiment shown, the transverse component of the flow results from the relative angular orientation between adjacent plates 42. This tortuous path promotes efficient heat transfer, allowing the micro miniature heat exchanger 28 to achieve the required temperature drop to enable the desired isenthalpic expansion through the Joule-Thomson flow restriction expansion element 30, ultimately producing the designed cooling temperature. Heat flow in this embodiment tends to be substantially radial.

FIG. 6 shows the preferred embodiment of the spacer 44, which is interspersed between the plates 42. The spacer 44 has an outer ring 45 and an inner ring 47 supported in the desired concentric relationship by spokes 70. An inner opening 72 within the inner ring 47 serves as a portion of the high pressure passageway 36 between plates 42. A plurality of outer openings 74 between the inner ring 47 and the outer ring 45 serve as a portion of the low pressure passageway 40 between plates 42. The inner ring 47 serves as a divider between the high and low pressure openings 72, 74.

FIG. 7 shows a second embodiment of the spacer 44' which can be used with a second embodiment of plates 42' shown in FIGS. 8 and 9. The spacer 44' has an outer ring 45' and a high/low pressure divider 47'. This divider 47' separates the high pressure opening 72' from the low pressure opening 74'. It can be seen that this spacer 44' can be turned over from the orientation shown in FIG. 7, to reverse the orientation of the divider 47', for reasons that will become apparent below. FIG. 8 shows a plate 42' having a relatively small rectangular high pressure hole 46' and a relatively large rectangular low pressure hole 48', with the long dimensions of the rectangular holes 46', 48' being vertically aligned. FIG. 9 shows the same type of plate 42', with the rectangular holes 46', 48' being arranged horizontally. These two hole patterns and the two spacer orientations possible with the spacer 44' are used to create a series of adjacent plates 42' and spacers 44' as shown in FIG. 10.

FIG. 10 shows this series arranged from left to right as they would be arranged from the proximal end of the heat exchanger toward the low pressure end, in successive series. The HP arrows show the flow path of the high pressure gas mixture into the plane of the page, while the LP arrows show the path of the low pressure gas mixture out of the plane of the page. FIG. 11 further illustrates this flow path, by showing a vertical section through the stacked plates 42' and spacers 44'. Dashed lines are used to show the locations of hidden high and low pressure holes. Here again, it can be seen that the gas mixture follows a tortuous path through both the high pressure and low pressure passageways 36, 40, but in this embodiment, the transverse components of the flow are much more pronounced than in the first embodiment, and the heat flow tends to be more axial than radial.

FIGS. 12 and 13 show yet another embodiment of the microminiature heat exchanger, constructed of rolled sheets, rather than stacked plates and spacers. The inner tube 24 of the catheter 18 is shown connected to a labyrinthine high pressure passageway 36' etched into a first sheet 76. A constriction is also etched into the outlet of the high pressure passageway 36', to form a Joule-Thomson expansion element 30'. A second sheet 80 has a low pressure passageway 40' etched therein, with an inlet 38' and an outlet 62'. Positioned in between the first sheet 76 and the second sheet 80 are spacer sheets 78 to separate the high pressure and low pressure passageways 36', 40'. The sheets 76, 78, 80 can be laminated in the orientation shown and diffusion bonded together, or joined by some other suitable process. The assembly is then rolled as shown in FIG. 13, to construct a cylindrical heat exchanger 28'.

Figure 14:
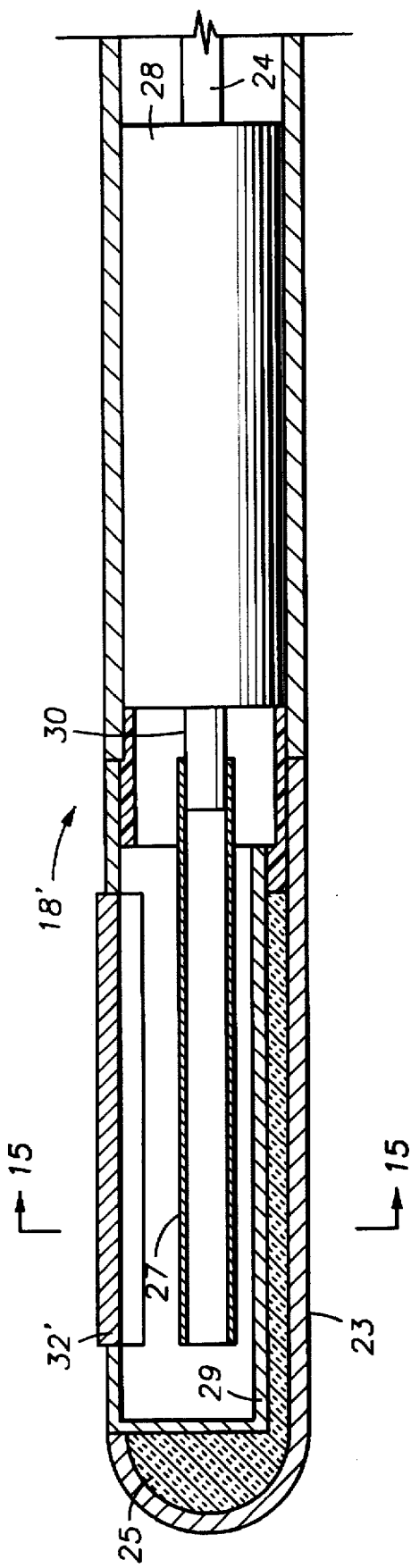
FIG. 14 is a partial section view of a second embodiment of the distal end portion of a cryosurgical probe, showing a narrow elongated heat transfer element.
Figure 15:
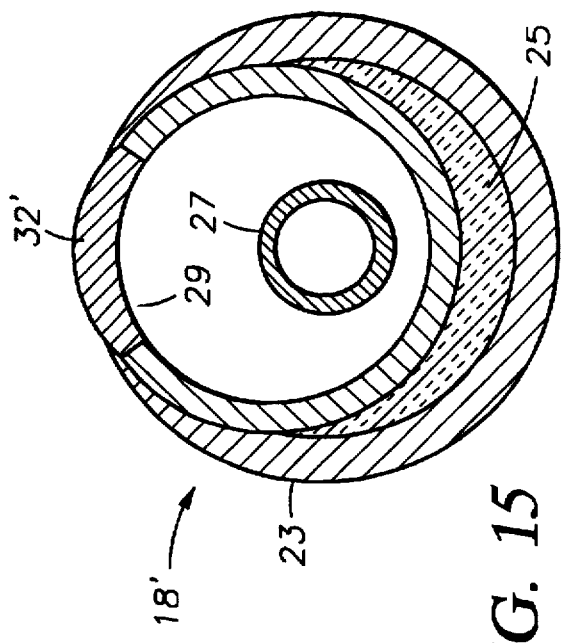
FIG. 15 is a section view of the second embodiment, taken along the line 15—15 in FIG. 14.
Figure 16:
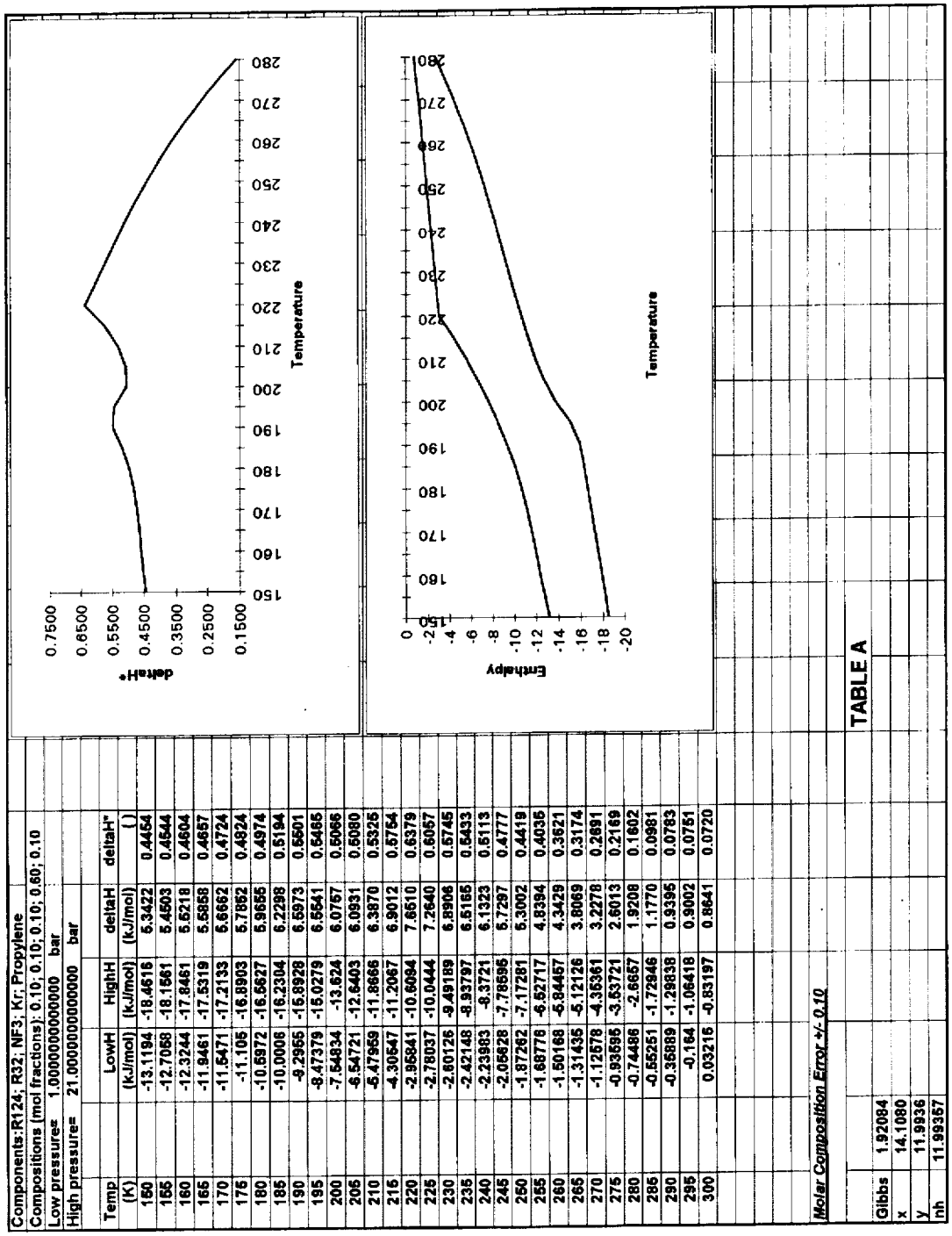
FIGS. 16 through 32 show enthalpy tables and graphs for seventeen fluid mixtures, for exemplary purposes.
Figure 17:
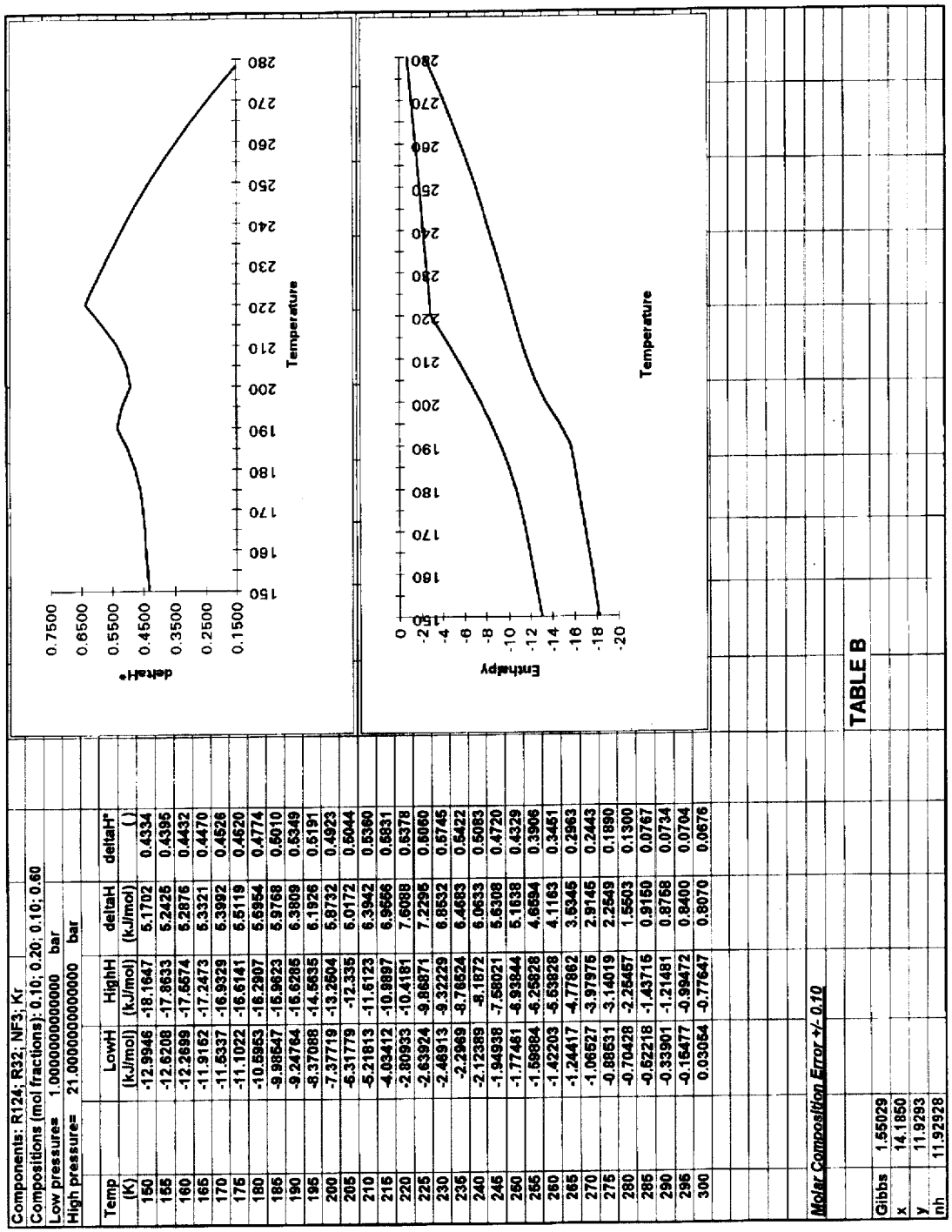
Figure 18:
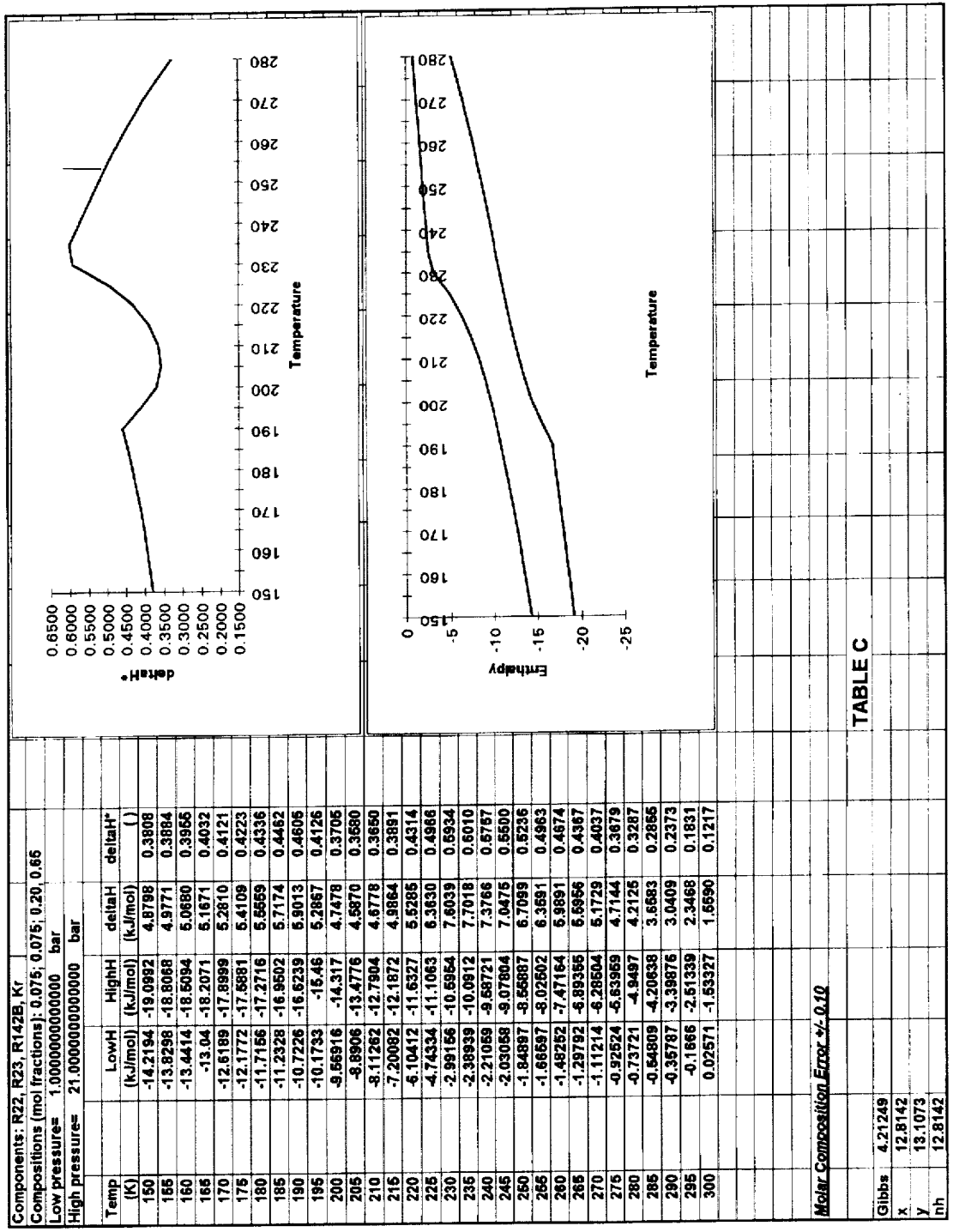
Figure 19:
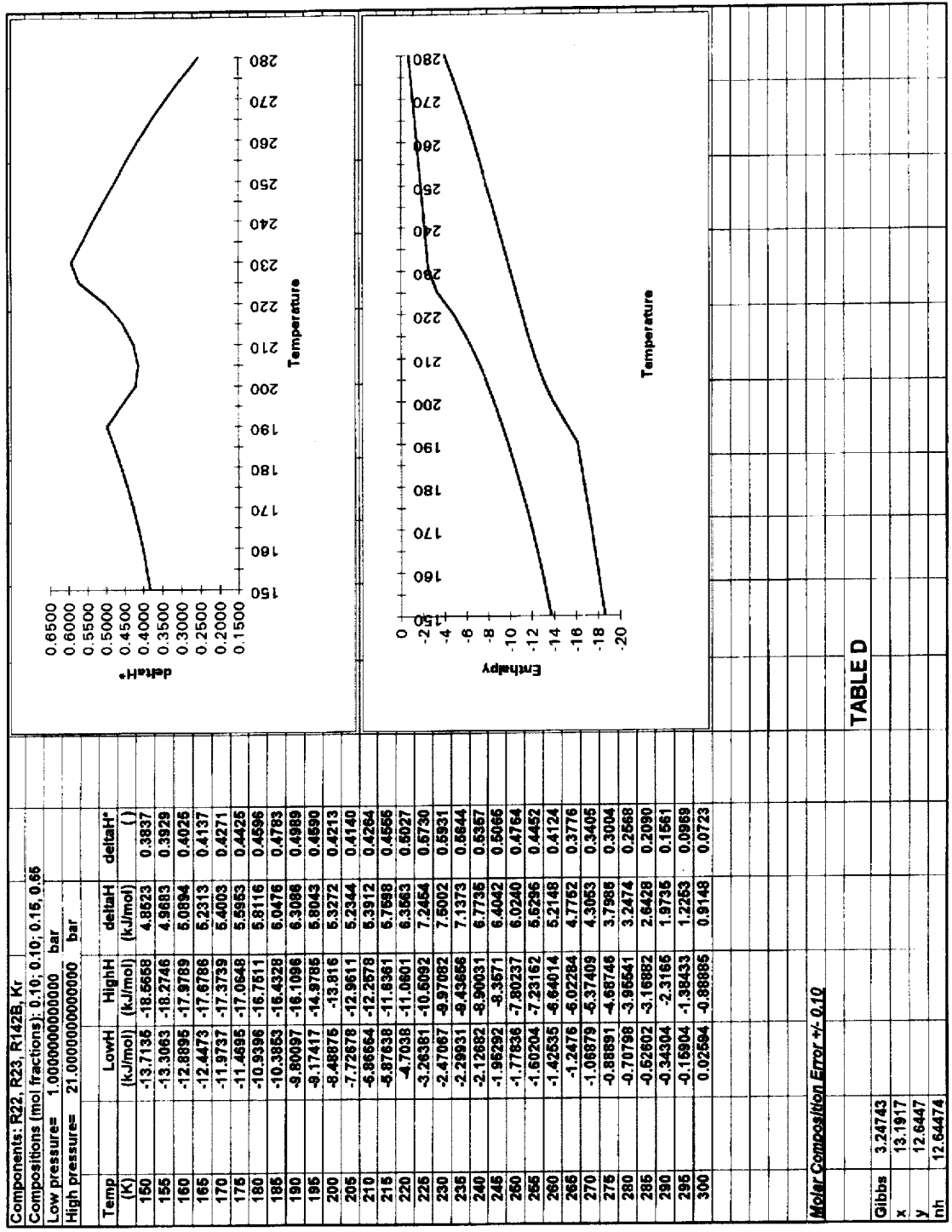
Figure 20:
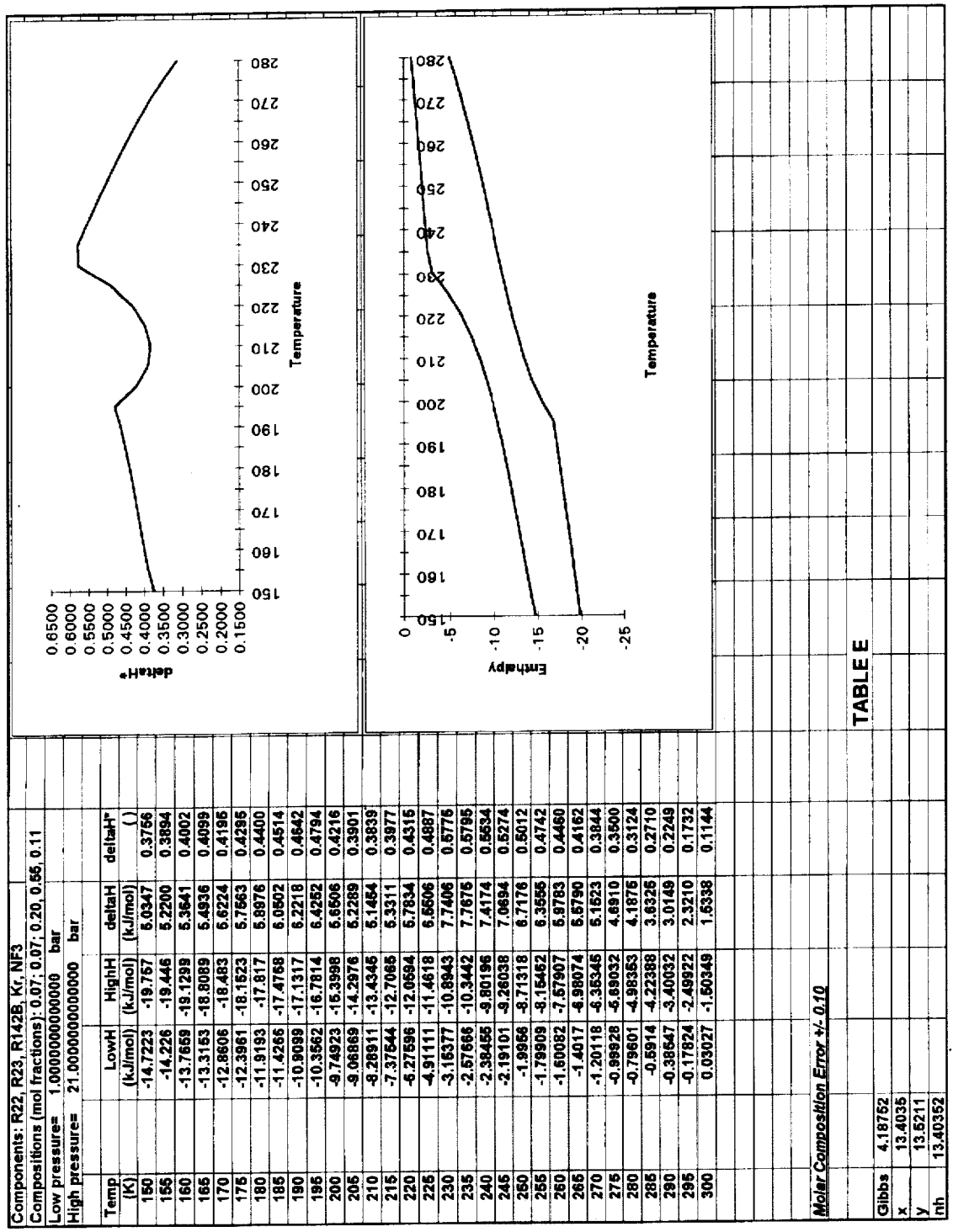
Figure 21:
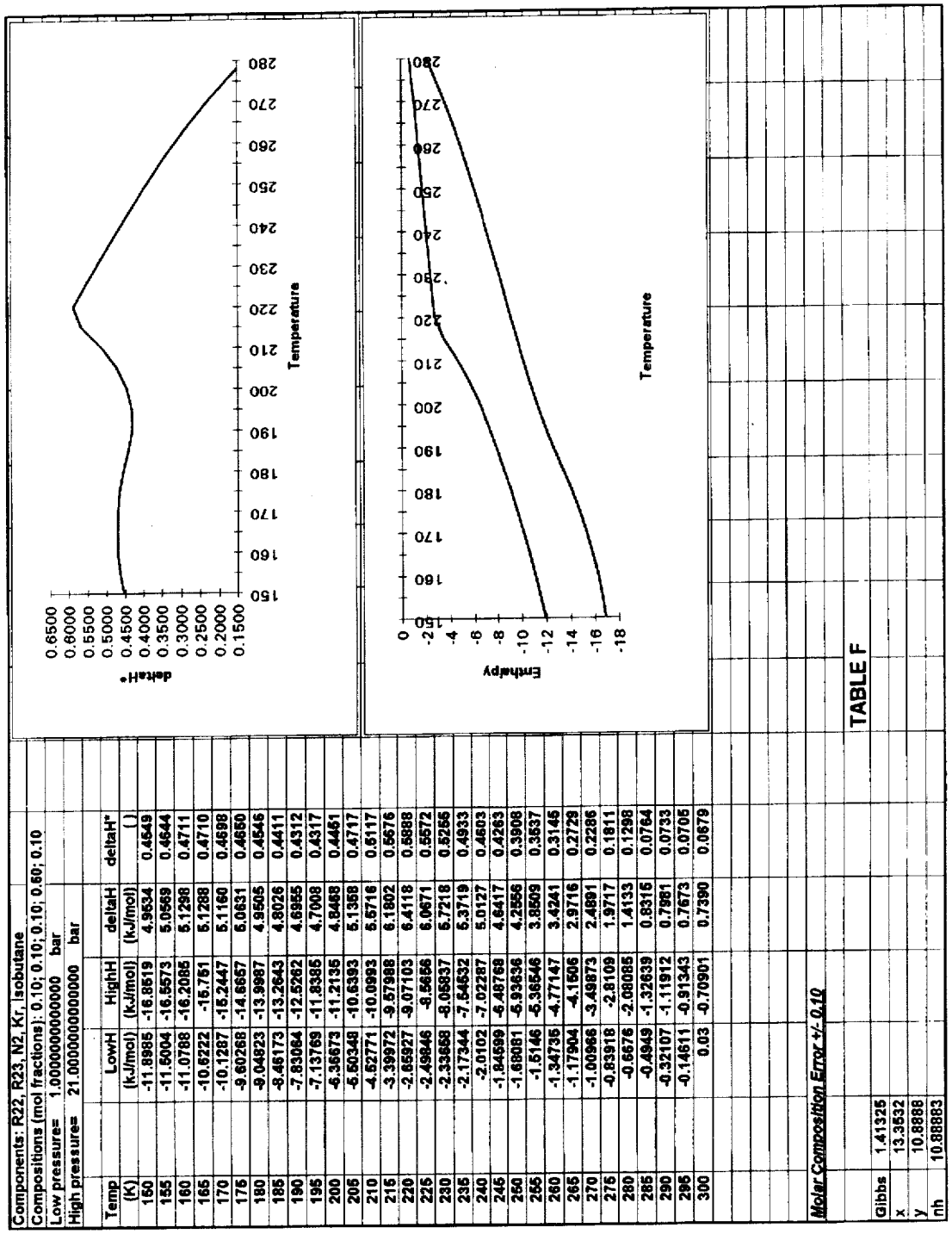
Figure 22:
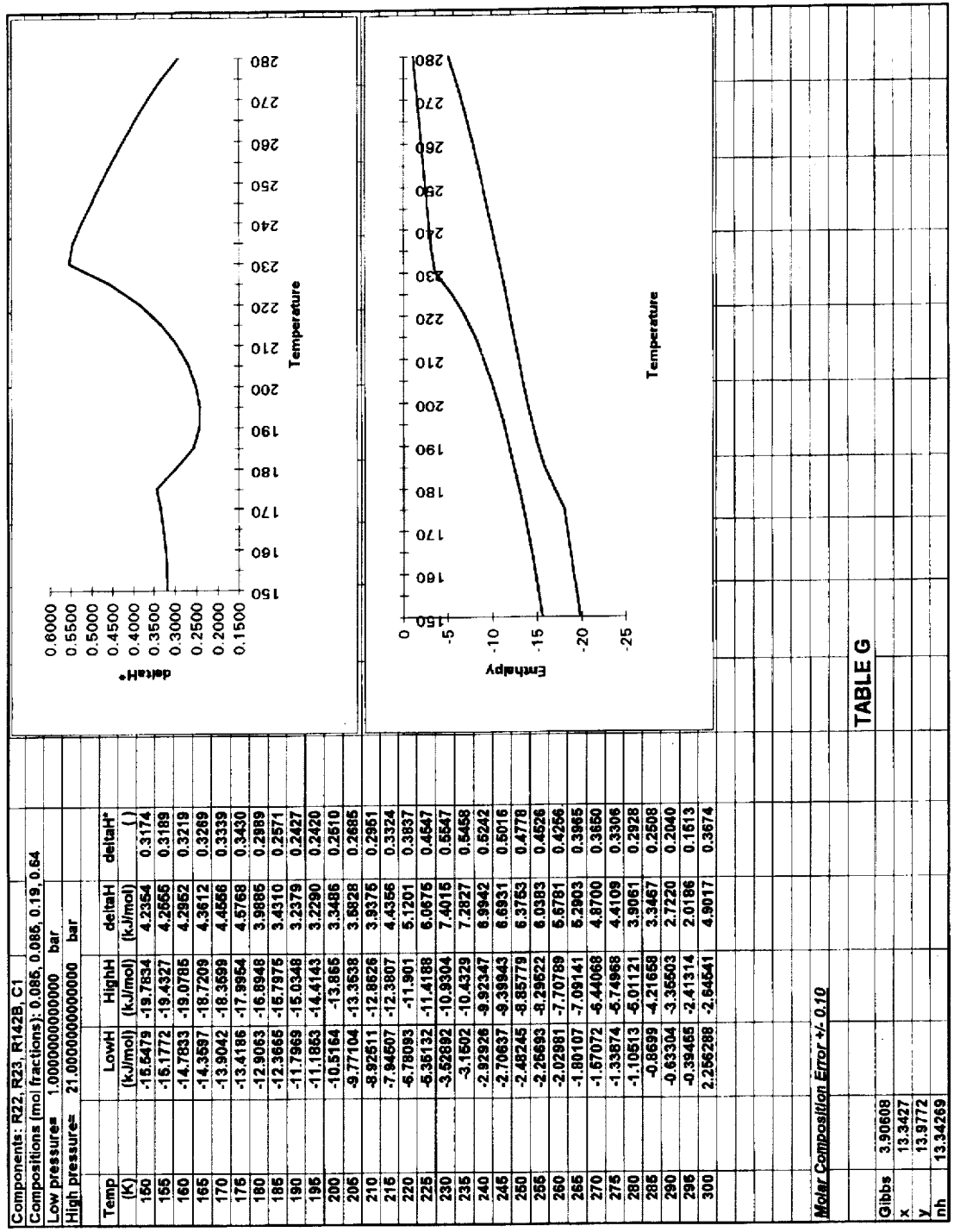
Figure 23:
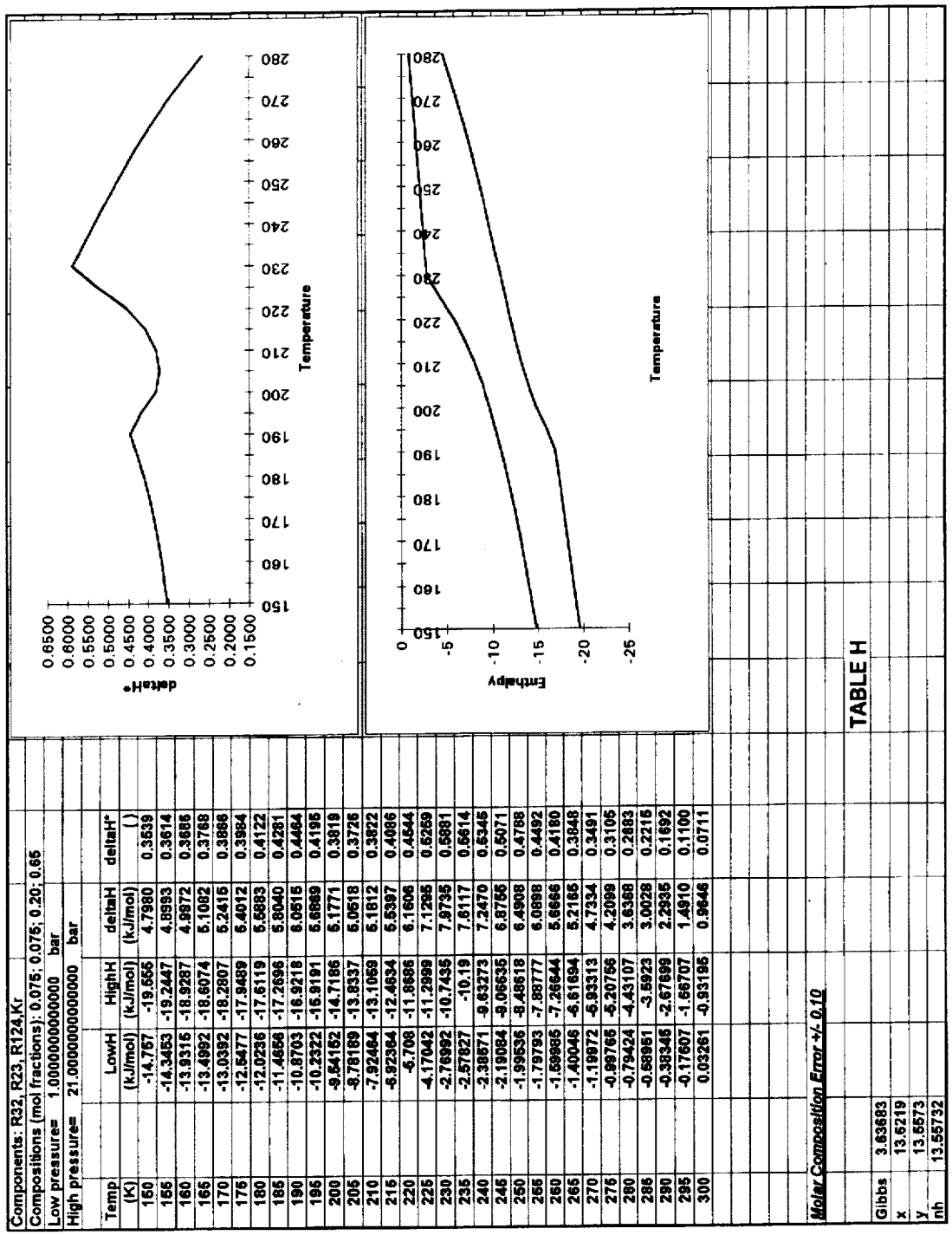
Figure 24:
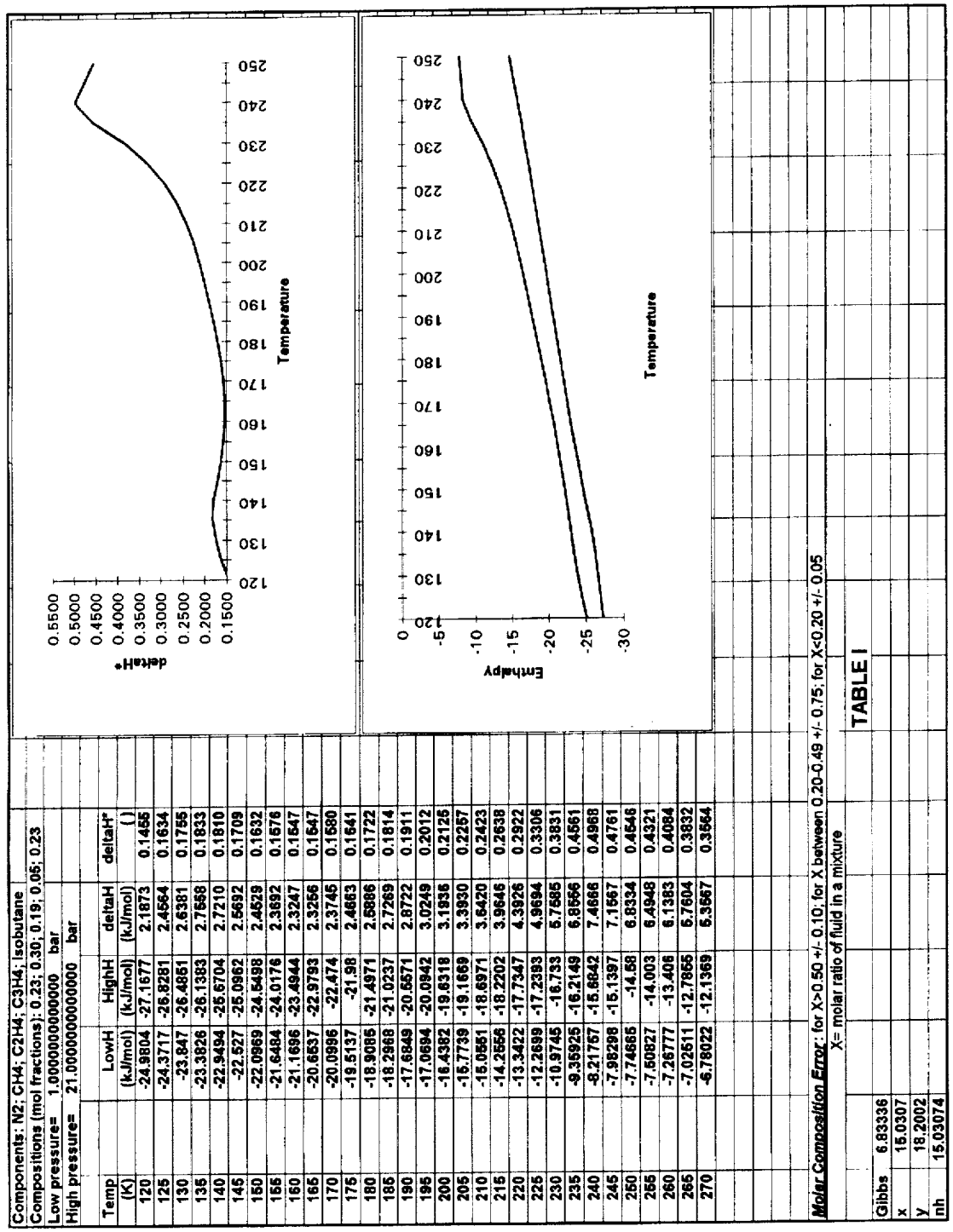
Figure 25:
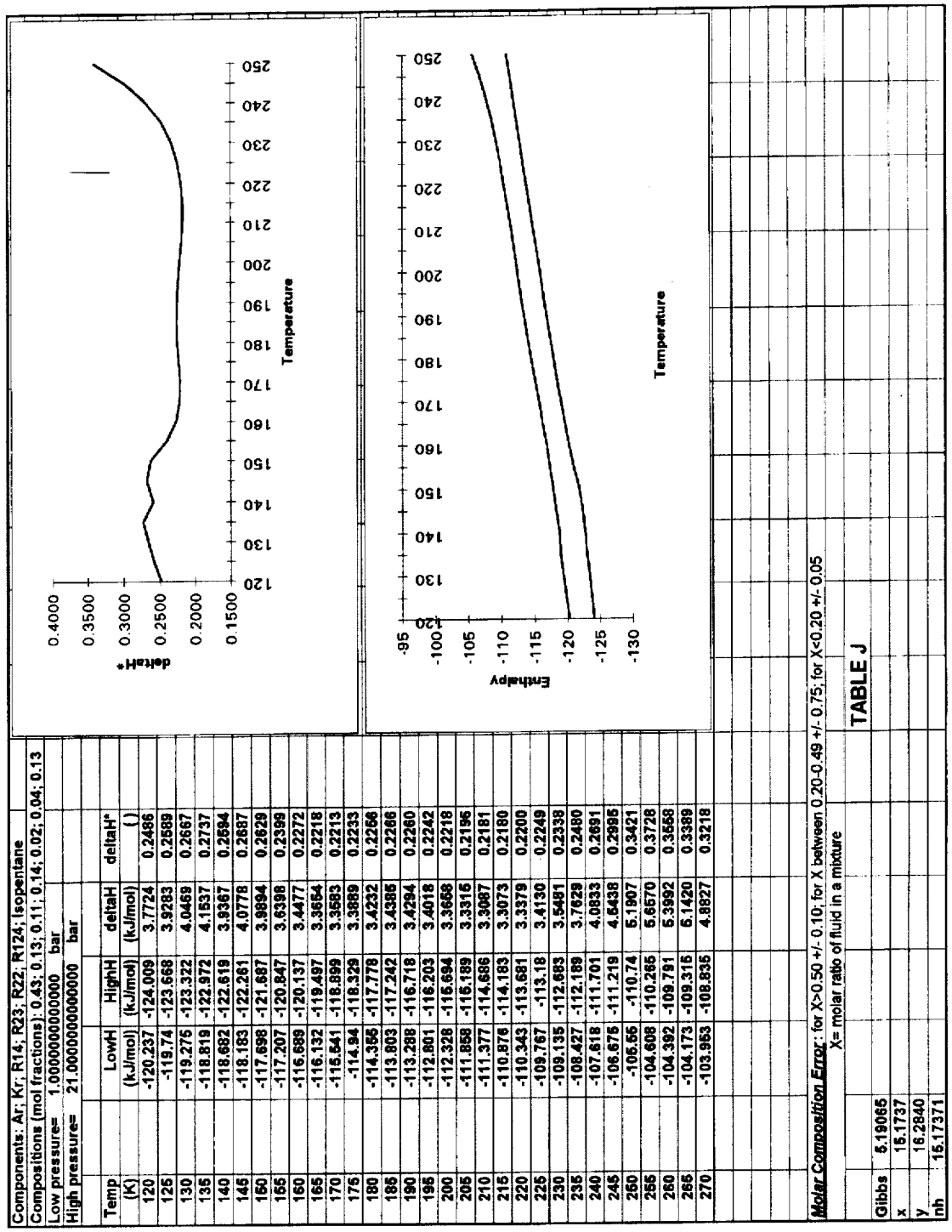
Figure 26:
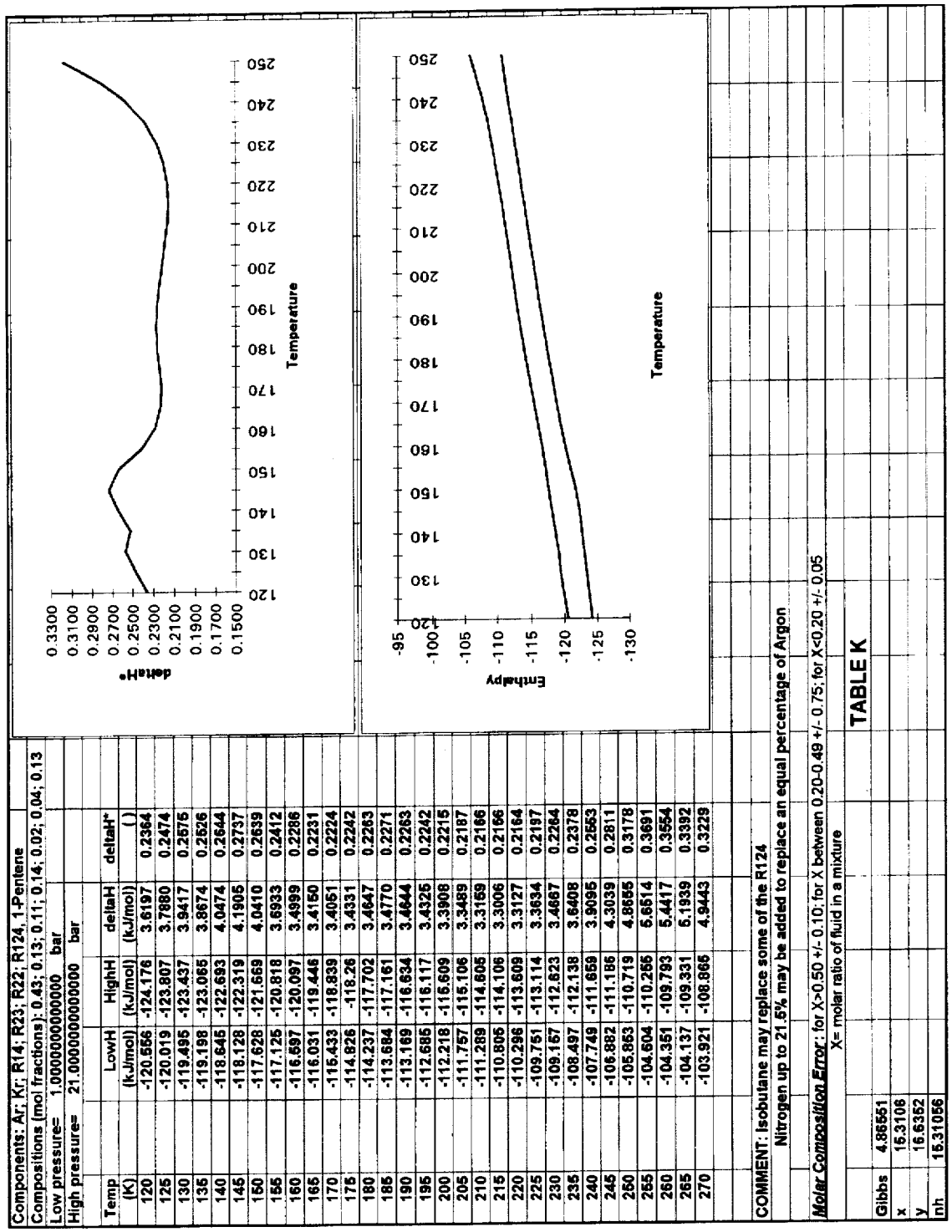
Figure 27:
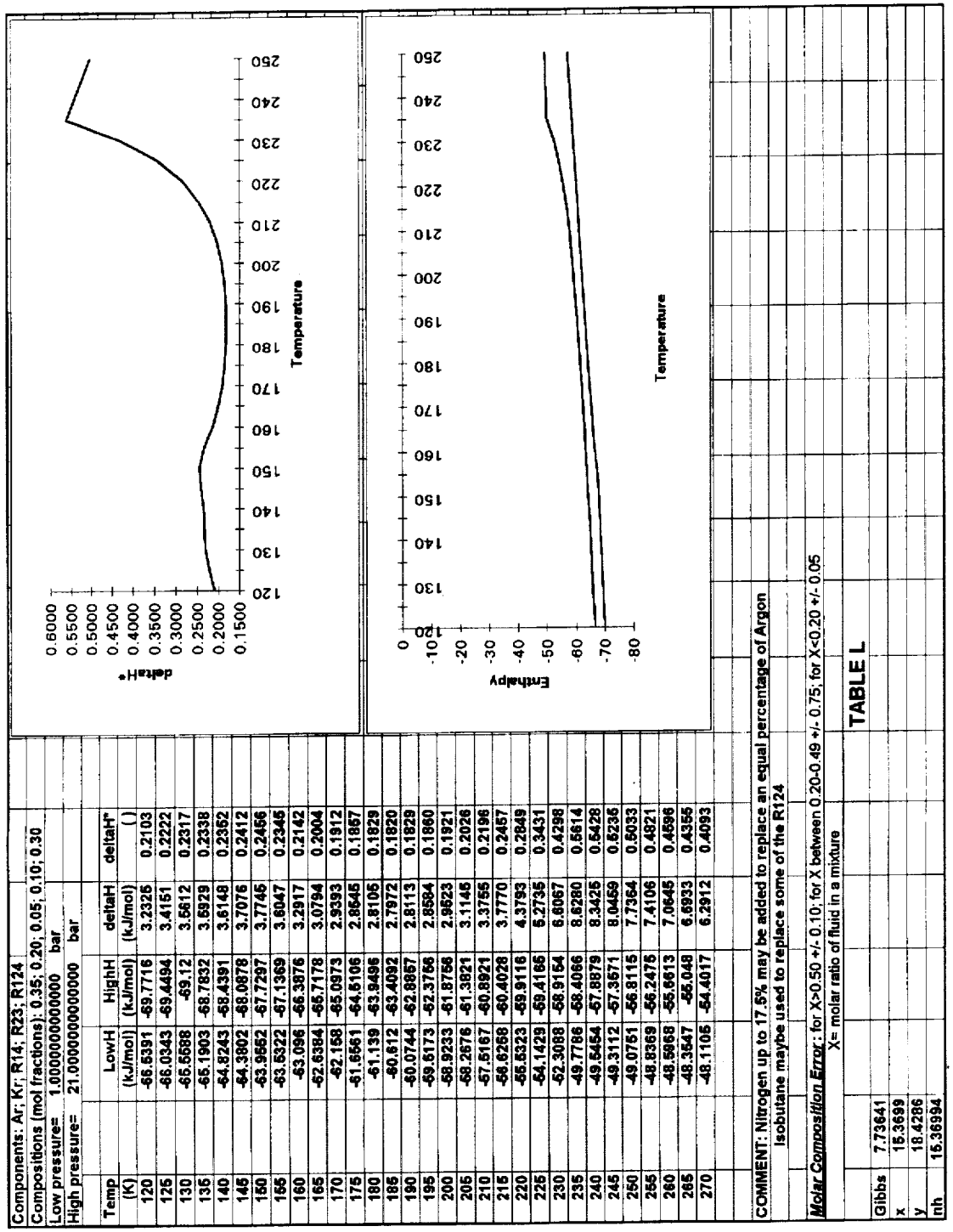
Figure 28:
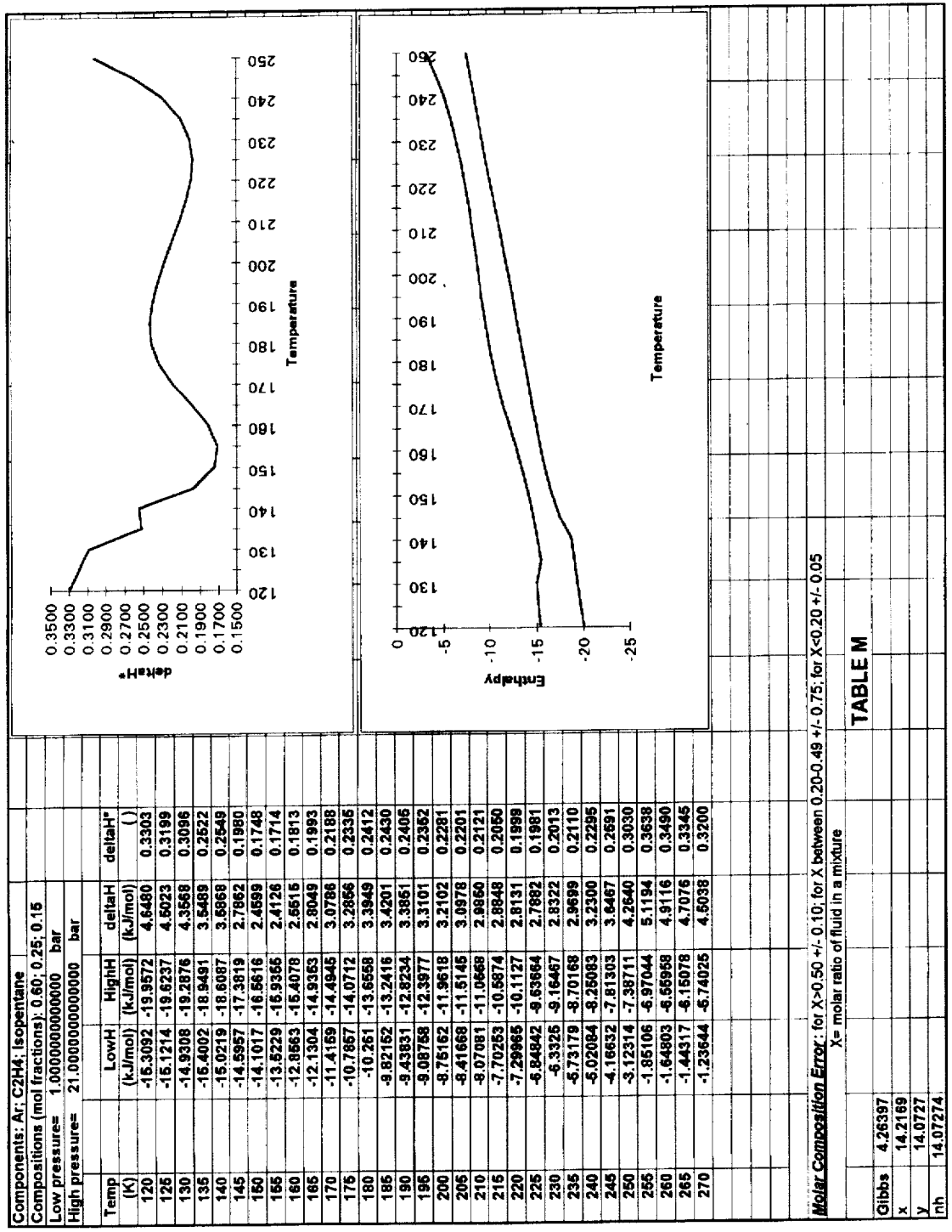
Figure 29:
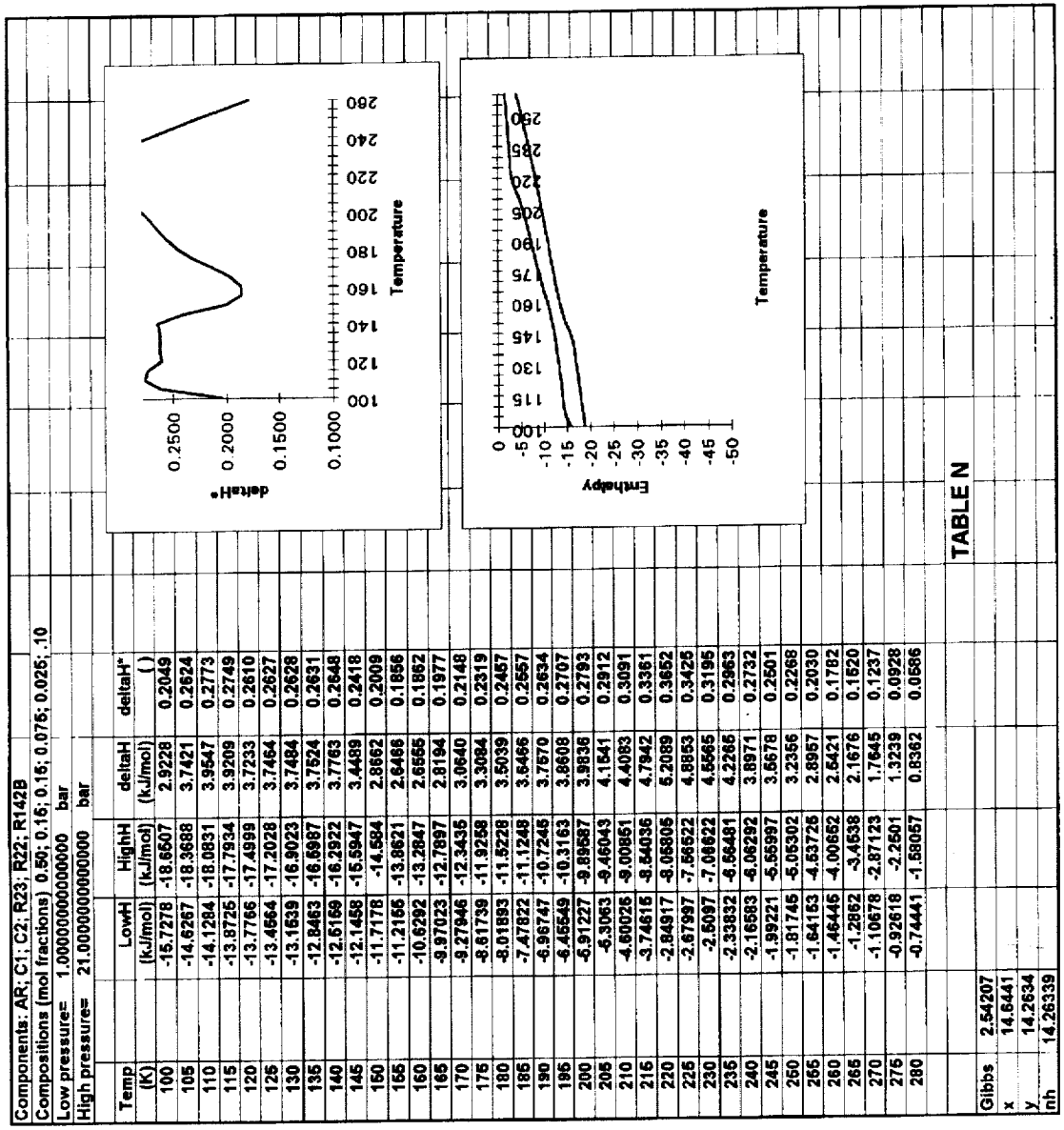
Figure 30:
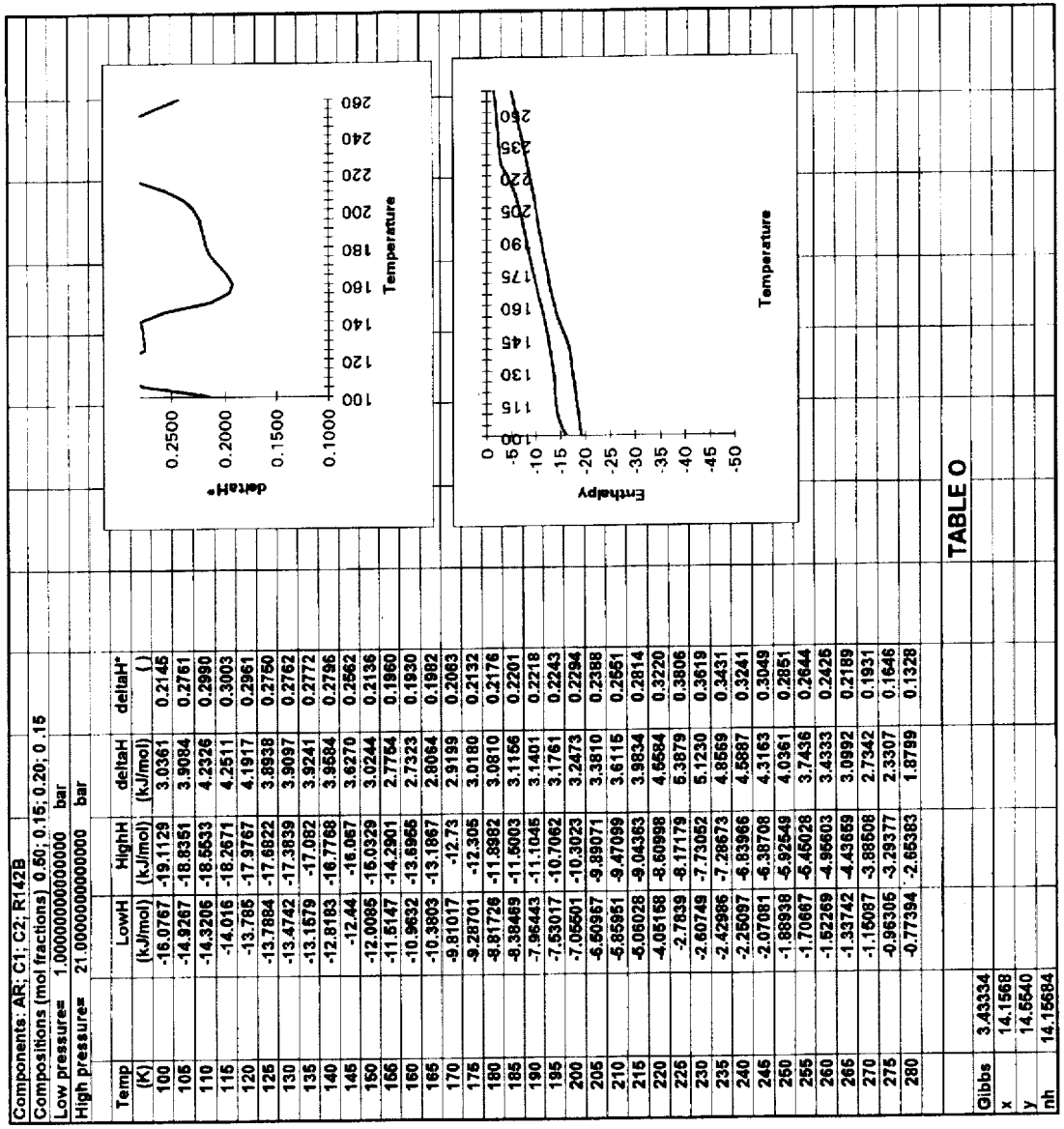
Figure 31:
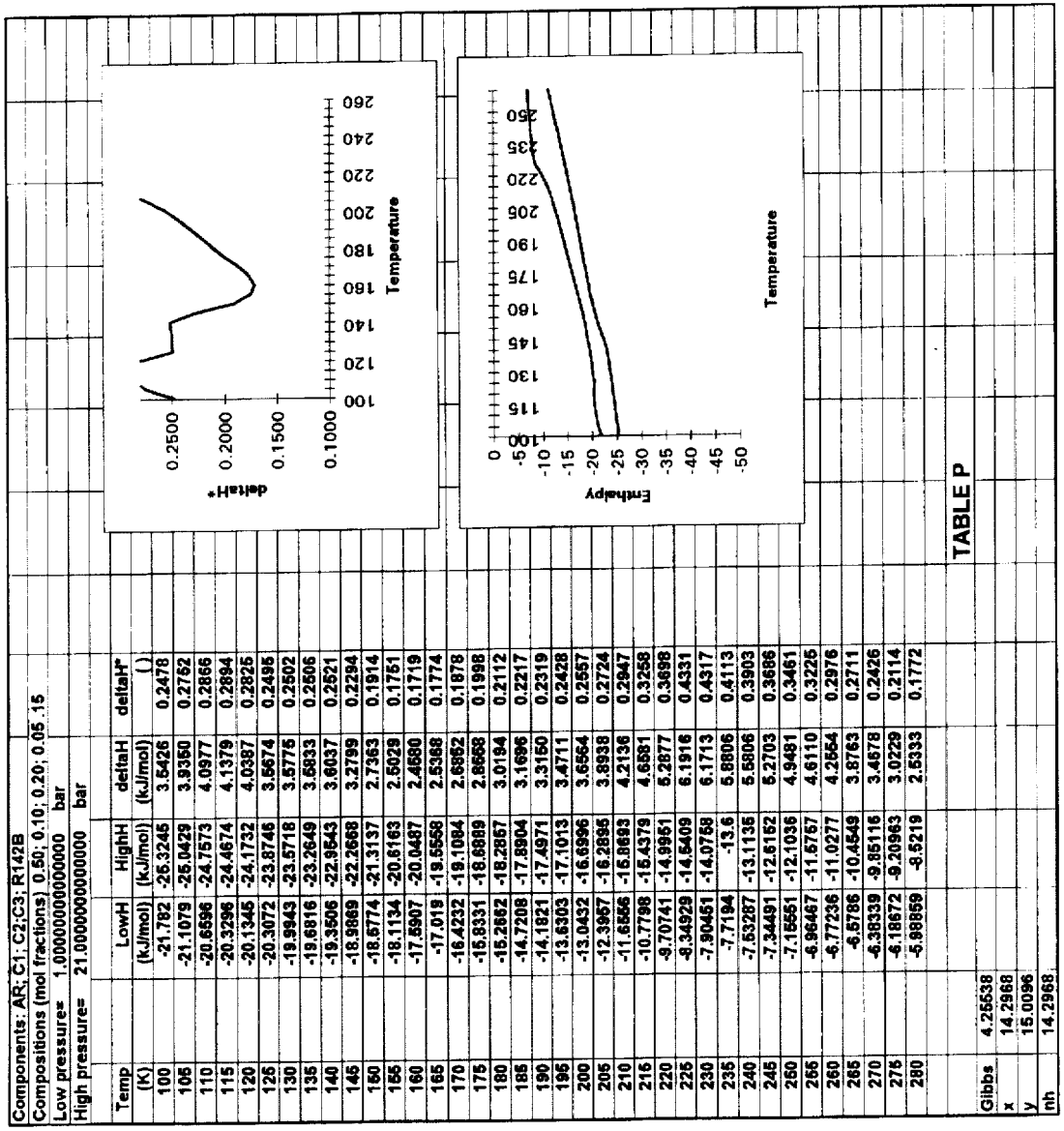
Figure 32:
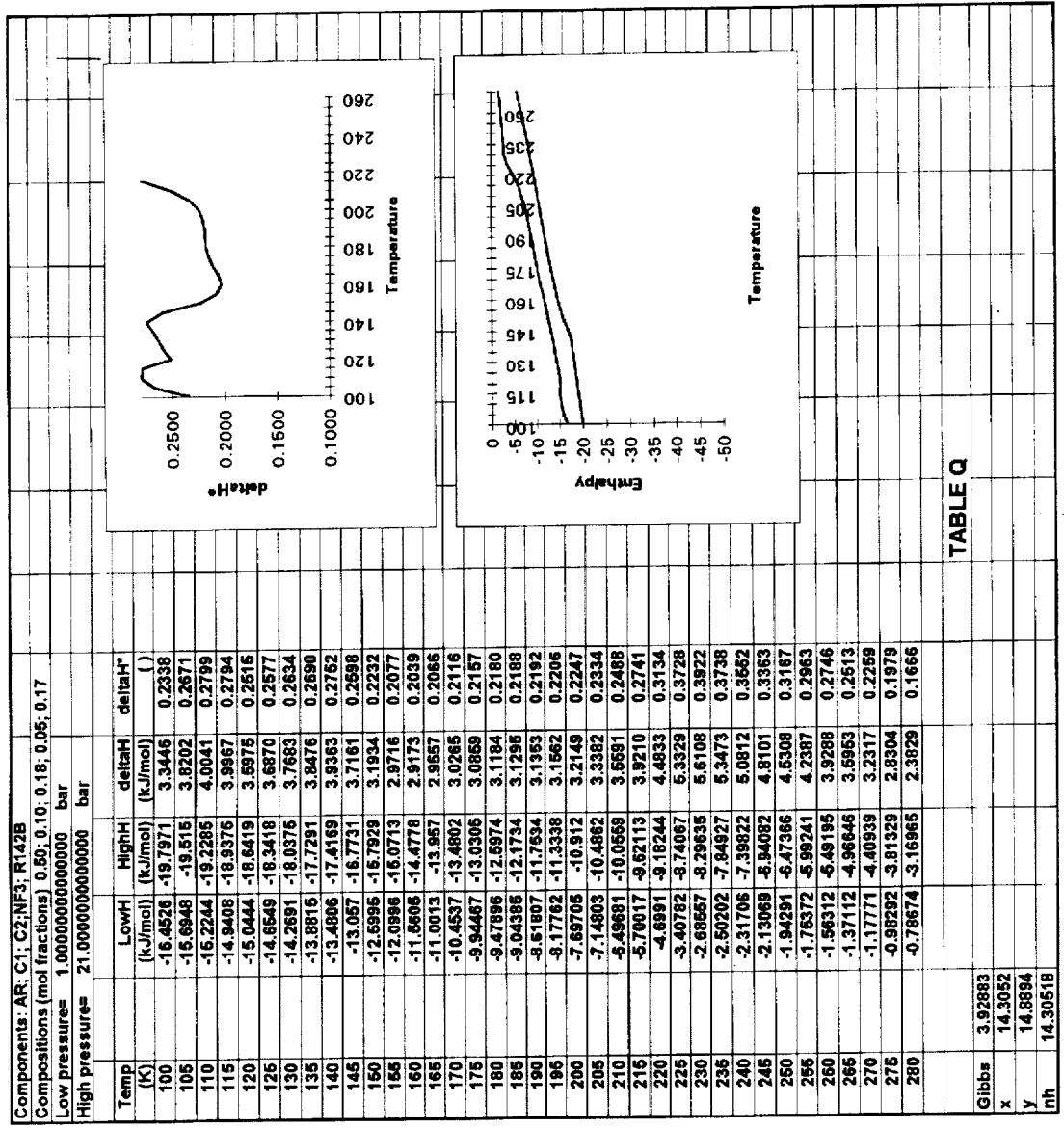

FIGS. 14 and 15 show a second embodiment of the distal end portion of the catheter 18', having a slender elongated heat transfer element 32'. This embodiment illustrates that the end portion of the catheter can have a fluid tube 27 affixed to the expansion element 30, a fluid chamber 29, and insulation 25 between the fluid chamber 29 and the extension tube 23. This construction insures that the cooling power is applied primarily through the heat transfer element 32'.

The size and inherent heat transfer capacity of the heat exchanger are limited, regardless of the design used. In the miniature environments envisioned for the use of this apparatus, space is at a premium. Whether used in a cardiac catheter or on a printed circuit board, therefore, severe size limitations will be placed upon the heat exchanger. For instance, a cardiac catheter must be introduced into, and maneuvered through a blood vessel to the target area for application of cooling. Therefore, a cardiac catheter necessarily is severely limited in diameter by the diameter of the blood vessels through which the catheter must pass. Further, the catheter must be highly maneuverable to be able to pass through the vascular system under the control of the physician. These maneuverability requirements call for the catheter to be somewhat flexible, especially near its tip, where the cold tip heat exchanger will be located. Unfortunately, most designs of the cold tip heat exchanger will probably be somewhat stiff, if not rigid. Therefore, the length of the heat exchanger must be severely limited, in order to leave the catheter in that region somewhat flexible. Limiting the size of the heat exchanger, of course, will result in a commensurate limitation of the amount of heat which can be transferred in the heat exchanger. This type of severe limitation on the size and capacity of the cold tip heat exchanger suggests that the overall refrigeration system be kept at the highest possible level of performance by the use of a secondary closed loop Joule-Thomson refrigeration system. When appropriate precooling is combined with the optimum gas or fluid mixture, the system will perform cooling as well as possible, in spite of the size limitations. The goal of this precooling system, in combination with the appropriate fluid mixture selection process, is to maximize the cooling power of the combination of the pre-cooling heat exchangers and the Joule-Thomson expansion elements.

For any particular gas mixture, and for any selected pressure range and temperature range, there is a theoretical limit to the amount of heat which can be transferred, even in a perfect heat exchanger. That limit is given by the equation $$Q_{hx} = n[h(P, T_h) - h(P, T_c)]_{min}$$

where n is the molar flow rate, h is the molar enthalpy, Th is the temperature at the hot end of a heat exchanger, $T_c$ is the temperature at the cold end of the heat exchanger, and P is the pressure, with the value of $Q_{hx}$ being calculated at both the high pressure and the low pressure. The subscript min denotes the fact that the value Of $Q_{hx}$ used is the lesser of the values computed at the two pressures.

Similarly, for that particular fluid mixture, and for that particular pressure and temperature range, there is a theoretical limit to the cooling power which can be achieved by even a perfect Joule-Thomson expansion element. That limit is given by the equation $$Q_r = n[h(P_l, T) - h(P_h, T)]_{min}$$

where $P_l$ is the low pressure, $P_h$ is the high pressure, and T is the temperature, with the value of $Q_r$ being calculated at a plurality of selected temperatures between the low and high temperatures at the extremes of the selected temperature range. The subscript$_{min}$ denotes the fact that the value of $Q_r$ used is the lowest of the values computed at the plurality of selected temperatures.

The ratio of the theoretical cooling power to the theoretical heat transfer capacity, or $Q_r/Q_{hx}$, can be thought of as a performance ratio which is characteristic of that particular fluid mixture, over that particular pressure and temperature range. The present invention includes a method for selecting a fluid mixture from among a group of candidate mixtures, which will have the highest performance ratio of any fluid mixture in the candidate group.

First, a list of pure component fluids is compiled, from which the candidate fluid mixtures will be formulated. Each component fluid might be an elemental fluid, or it could be a compound of several elements. Each component fluid might be either organic or inorganic. One requirement is that the fluid mixture must have a triple point below the lowest temperature in the selected temperature range, to prevent freezing of the fluid mixture in the apparatus. This requirement can be met by ensuring that each component fluid in the list has a triple point below the lowest temperature to be encountered. Alternatively, some of the component fluids can have triple points within the anticipated temperature range, as long as the triple point of each of the formulated fluid mixtures has a triple point below the anticipated temperature range. A second requirement is that each fluid mixture must have a positive Joule-Thomson coefficient; in other words, a pressure drop in the fluid mixture must be accompanied by a temperature drop. One way of ensuring this is to ensure that each of the component fluids on the list has a positive coefficient. Alternatively, some component fluids could have negative coefficients, as long as the coefficient of each fluid mixture has a positive coefficient.

For each of the component fluids in this list, the molar enthalpy must be known at a plurality of data points over the selected range of temperatures and the selected range of pressures, with these selected ranges being the temperature and pressure ranges at which the fluid mixture will be pumped through the refrigeration apparatus.

Then, a plurality of mixtures of the component fluids are selected, with each fluid mixture having a number of component fluids, and with each component fluid being present in a particular molar fraction. Any number of component fluids could theoretically be included in a fluid mixture. In actual practice, of course, computation capabilities will require that some limit be placed on the highest possible number of component fluids included in any one fluid mixture. Two fluid mixtures having the same component fluids, but with the component fluids being present in different molar fractions, would be considered two different fluid mixtures. As few as two candidate fluid mixtures might be selected for comparison in the simplest case. However, any number of mixtures might be formulated, up to the maximum number that can be formulated from the component fluids under consideration. Based upon the known thermodynamic properties of each of the component fluids, the molar enthalpy of each formulated fluid mixture is then calculated at a plurality of data points over the selected range of temperatures and the selected range of pressures.

One known method of calculating the molar enthalpy of each fluid mixture at a plurality of data points over the selected temperature and pressure ranges is the extended corresponding states method as used in Mixture Property Database (DDMIX) program and the Thermophysical Properties of Hydrocarbon Mixtures (SUPERTRAPP) program, both available from the National Institute of Standards and Technology (NIST). Enthalpy values and other thermophysical properties of the candidate fluid mixtures can be estimated, with the aid of these programs, through the use of approximate shape factors based on saturation boundary matching. A reference fluid is typically selected, with the thermophysical properties of the other fluids being given in relation to the properties exhibited by the reference fluid. The refrigerant R134 has been found to serve as an appropriated reference fluid for these computations, but other fluids could also serve.

The component fluids selected must have a triple point below the low end of the selected temperature range, to eliminate the possibility of the formation of solids. The database of component fluids can contain refrigerants, light hydrocarbons including alkanes and alkenes, and noble gases, including argon, krypton, and neon. The phase split and enthalpy content of each selected candidate fluid mixture are computed as a function of temperature and pressure.

For each candidate fluid mixture, a series of calculations are then performed. It can sometimes be assumed that the pressure drop through the heat exchanger, on either the high pressure side or the low pressure side, is negligible. Alternatively, if an appreciable pressure drop is anticipated, a starting pressure can be selected which will take into account the pressure drop in the heat exchanger. For the low pressure in the selected pressure range, the molar enthalpy of the fluid mixture at the low temperature in the selected temperature range is subtracted from the molar enthalpy at the high temperature in the range, yielding a low pressure enthalpy difference between the fluid mixture states at the two temperatures. Similarly, for the high pressure in the selected pressure range, the molar enthalpy at the low temperature is subtracted from the molar enthalpy at the high temperature, yielding a high pressure enthalpy difference between the fluid mixture states at the two temperatures. The lesser of these two enthalpy differences is the theoretical molar enthalpy difference which could be achieved in a perfect counterflow heat exchanger operating with the selected fluid mixture over the selected temperature range and pressure range. The theoretical heat transfer capacity of such a heat exchanger with the selected fluid mixture, over the selected temperature and pressure range, is the product of the molar flow rate of the fluid mixture and this theoretical molar enthalpy difference. The theoretical heat transfer capacity is calculated for each candidate fluid mixture.

Then, a plurality of temperatures are selected at uniform increments over the selected temperature range. The number and size of the temperature increments can vary. A temperature increment of 5 degrees is often satisfactory. As an example, if the selected temperature range is from 120K to 270K, and if the size of the increment is set at five degrees, this results in a total of 30 increments, and 31 selected temperatures. For each candidate fluid mixture, the molar enthalpy of the fluid mixture at the high end of the selected pressure range is subtracted from the molar enthalpy at the low end of the pressure range, yielding a molar enthalpy difference between the fluid mixture states at the two pressures. This calculation is performed at each of the 31 selected temperatures. The higher the number of selected temperatures used, and the smaller the size of the increments, the greater will be the usefulness of the information calculated. The molar enthalpy difference calculated at each of these selected temperatures is the theoretical enthalpy increase which would occur during expansion of the candidate fluid mixture from the high pressure to the low pressure, at that temperature, if the temperature were to remain constant.

In Joule-Thomson expansion, however, there is very little or no opportunity for heat transfer to or from the fluid as it flows through the expansion element, no change in potential energy of the fluid, no work performed, and very little or no change in kinetic energy of the fluid. Therefore, the enthalpy states of the fluid before and after the expansion are essentially the same. As the pressure sharply decreases during expansion, the temperature of the fluid also sharply decreases, maintaining an essentially constant enthalpy. This colder fluid then can be used to cool the surroundings. In actuality, then, the temperature does not remain constant during expansion, and the theoretical cooling power available through Joule-Thomson expansion of the candidate fluid mixture, in the selected temperature range, is a function of the lowest theoretical enthalpy difference at any of the selected temperatures. More specifically, the theoretical cooling power available through Joule-Thomson expansion of the candidate fluid mixture is the product of the molar flow rate of the fluid mixture and the lowest theoretical molar enthalpy difference calculated at any temperature over the selected temperature range. The theoretical cooling power is calculated for each candidate fluid mixture.

Therefore, each candidate fluid mixture in the group exhibits a theoretical cooling power and a theoretical heat transfer capacity, over the selected temperature and pressure range. The ratio of the theoretical cooling power to the theoretical heat transfer capacity can be called a performance ratio which is characteristic of that particular fluid mixture over that temperature and pressure range. In order to optimize the operation of the apparatus of the present invention, a fluid mixture is chosen from among the candidate mixtures, which will result in the highest performance ratio. That is the optimum fluid mixture, among that group of candidates, within the temperature and pressure ranges selected. It can be seen that, if the performance ratio is equal to or greater than unity, meaning that the theoretical cooling power is as great as the theoretical heat transfer capacity, then the maximum cooling possible over the desired temperature and pressure range can be achieved through Joule-Thomson expansion alone, and no heat exchanger is needed. If the highest performance ratio in the group is less than unity, at least one heat exchanger will be required.

FIGS. 16 through 32 show Tables A through Q of enthalpy values of various fluid mixtures, derived through the extended corresponding states method. The component fluids used in formulating the candidate fluid mixtures were Ar, $CH_4$, $C_2H_4$, $C_3H_4$, Kr, $N_2$, $NF_3$, 1-pentene, Isobutane, Isopentane, Propylene, R14, R22, R23, R32, R124, and R142b. It has been found that various mixtures of these component fluids can be useful in the operation of miniature mixed gas refrigeration systems. The enthalpy values in each table are shown at a low pressure of 1.0 bar in the column labeled Low H, and at a high pressure of 21.0 bar in the column labeled High H. Based upon these enthalpy values, calculations are made to arrive at calculated values of delta H at each incremental temperature. Then, according to a method described below, based upon the selected temperature range, values of delta H* are calculated at each incremental temperature. In addition to the table of enthalpy and related values, each Figure also shows a graph of delta H* vs. temperature, and a graph of Low H and High H vs. temperature. Tables A through H show enthalpy values and delta H* between 150K and 300K, with the selected temperature range of interest being from 150K to 270K. Tables I through M show enthalpy values and delta H* between 120K and 270K, with the selected temperature range of interest being 120K to 270K. Tables N through Q show enthalpy values and delta H* between 100K and 280K, with the selected temperature range of interest being 100K to 260K.

The temperature ranges covered by the tables were arbitrarily selected to demonstrate that the enthalpy values for a mixture can be given over any desired temperature range, with the delta H* values in a given table being calculated based upon the selected temperature range of interest. Comparisons between fluid mixtures can be taken only from tables which have delta H* values calculated based on the same selected temperature range. For instance, all of the tables include enthalpy values over the range of 150K to 270K. However, only Tables A through H can be used for comparing calculated values of delta H* based upon a selected temperature range of 150K to 270K, because the values of delta H* in the other tables were calculated based upon a different selected temperature range.

Similarly, Tables I through Q all show enthalpy values over the range of 120K to 270K, but only Tables I through M can be used for comparing calculated values of delta H* based upon this selected temperature range. This is because the calculated values of delta H* in Tables N through Q were calculated based upon a selected temperature range of 100K to 260K. Listed values of delta H* which are outside the selected temperature range for a given table are calculated by the method of the present invention and shown in the table, but they are not pertinent to the selection of a fluid mixture for use within the selected temperature range.

The following discussion will specify selected temperature ranges which are covered by the tables referenced. In all cases, the temperature increments are 5 Kelvin degrees. H is molar enthalpy. The values of thermophysical properties are referenced to the values for R134a. Each table lists the molar enthalpy values of the candidate fluid mixture at increments of 5 degrees, for a low pressure of 1.0 bar, and for a high pressure of 21.0 bar. Further, for each incremental temperature over the range, a delta H is given, with delta H being the difference between the enthalpy values at the low pressure and the high pressure at that temperature.

For the low pressure, on a given table, it can be seen that the enthalpy value at the low temperature in the selected range can be subtracted from the enthalpy value at the high temperature in the selected range, to give a low pressure enthalpy difference. This is the y value shown near the lower left hand corner of the table. A similar calculation can be performed for the high pressure, yielding a high pressure enthalpy difference. This is the x value shown near the lower left hand corner. The lesser of the low pressure enthalpy difference and the high pressure enthalpy difference is the theoretical enthalpy difference available over that selected temperature range. This is the nh value shown near the lower left hand corner. The molar Gibbs free energy is also shown.

For each incremental temperature, if the value shown in the delta H column is divided by the theoretical enthalpy difference, nh, the result is shown in the column designated delta H*. Since the theoretical enthalpy difference, nh, is based upon a selected temperature range, the calculated values of delta H* are based upon that range, as well. The lowest value of delta H* within the selected temperature range, for any given table, is the same as the theoretical cooling power divided by the theoretical heat transfer capacity, since the molar flow rate is the same in both terms. This value, delta $H^*_{min}$, is the performance ratio for that fluid mixture, over the selected temperature range.

By way of example, select a temperature range of 120K to 270K, and a pressure range of 1.0 bar to 21.0 bar. Tables I through M contain delta H* values for five fluid mixtures over this selected temperature range. Over this selected temperature range, the fluid mixture having the highest value of delta $H^*_{min}$ is addressed in Table J, and the value of delta $H^*_{min}$ for that fluid mixture is 0.2180. This means that, of the fluid mixtures addressed in the tables which show calculated delta $H^*$ values based upon a selected temperature range of 120K to 270K, over this selected temperature and pressure range, the optimum fluid mixture is 43% Argon, 13% Krypton, 11% R14, 2% R22, 14% R23, 4% R124, and 13% Isopentane. In Tables I through M, the molar composition values of 50% or higher have a possible error of ±10%, values from 20% to 49% have a possible error of ±7.5%, and values below 20% have a possible error of ±5%.

By way of a further example, select a temperature range of 150K to 270K. Tables A through H contain delta $H^*$ values calculated for seven fluid mixtures based upon this range. For the fluid mixtures addressed in the tables which show calculated delta $H^*$ values over this range, the fluid mixture having the highest value of delta $H^*_{min}$ is addressed in Table E, and the value of delta $H^*_{min}$ for that fluid mixture is 0.3756. This means that, of the fluid mixtures addressed in these tables, over this selected temperature and pressure range, the optimum fluid mixture is 7% R22, 7% R23, 20% R142b, 55% Krypton, and 11% $NF_3$. In Tables A through H, the molar composition values have a possible error of ±10%.

Use of the tables can be further illustrated by showing a means of eliminating toxicity or flammability in the selected gas mixture. Noting that $NF_3$ is potentially toxic to humans, for instance, the fluid mixture used in the last example may not be desirable for use in a mixed gas refrigeration system which will be used in a heart catheter. A fluid mixture which is similar, but which does not include this component fluid is addressed in Table C. It can be seen that the value of delta $H^*_{min}$ for that fluid mixture over the same selected temperature range is 0.3580. This means that, of the fluid mixtures addressed in these tables, over this selected temperature and pressure range, the optimum non-toxic fluid mixture is 7.5% R22, 7.5% R23, 20% R142b, and 65% Krypton. Toxicity or flammability can therefore be eliminated by a slight change in the gas mixture selected.

It can be seen that, for some of the primary fluid mixtures addressed in the tables, the minimum value of delta $H^*$ occurs in the upper part of the selected temperature range. For such a fluid mixture, pre-cooling of the primary fluid mixture with a secondary refrigeration system can lower the top end of the temperature range to a level which results in a higher value of delta $H^*_{min}$ as the primary mixture flows through the primary expansion element.

For example, consider the possibility of using a pre-cooler to lower the temperature of the fluid mixture from 270K to 260K prior to introducing the mixture into the catheter. The mixture addressed in Table B will show a proportional increase in delta $H^*_{min}$ of over 40%, which is almost twice the proportional increase of over 20% which would result in the mixture addressed in Table D. Therefore, in systems where it is possible to pre-cool the fluid mixture before introducing it into the micro miniature heat exchanger, and where it is desirable to use that pre-cooling to control the performance of the system, the mixture in Table B might be more advantageous.

It should be noted that gases with similar boiling points are interchangeable in a selected fluid mixture. For example, R124 can be substituted in the place of R142b or Isobutane, and Nitrogen can be substituted in the place of Argon. The substitution can be at an equal, or slightly different, percentage, with only slight changes in delta $H^*_{min}$. A good example of this can be seen by examining Tables C and H.

The mixture in Table C is 7.5% R22, 7.5% R23, 20% R142b, and 65% Krypton, with a delta $H^*_{min}$ of 0.3580. In the mixture addressed in Table H, $R_{32}$ has been substituted in place of $R_{22}$, and $R_{124}$ has been substituted in place of $R_{142}b$, to arrive at an environmentally safer mixture, but the delta $H^*_{min}$ has only dropped to 0.3491, a drop of only about 2%.

Figure 33:
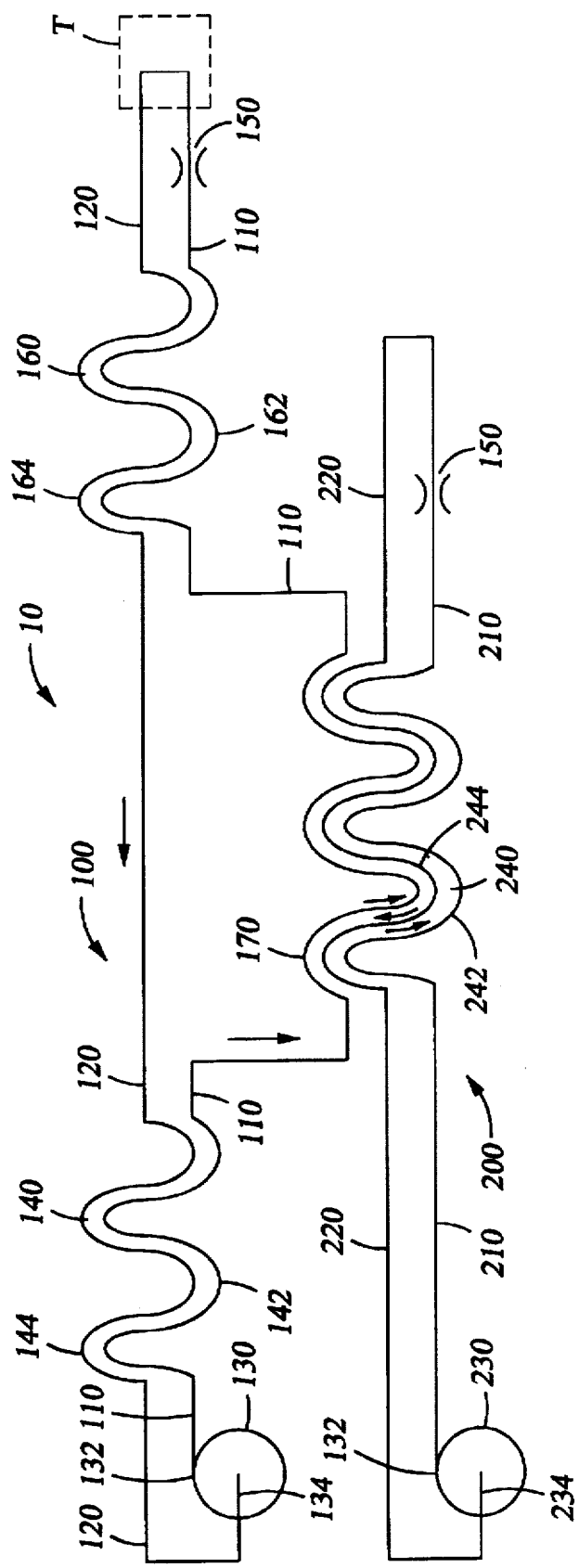
FIG. 33 is a schematic of the primary and secondary closed loops of the present invention.

FIG. 33 shows a schematic of the dual closed loop refrigeration system 10 of the present invention, incorporating the pre-cooling concept. The primary loop 100 is similar in some respects to the primary loop described above in the non-precooled system. The secondary loop 200 has been added for the purpose of maximizing the pre-cooling effect. The primary loop 100 consists of a high pressure path 110 and a low pressure path 120. A primary loop compressor 130 compresses the primary gas mixture to a selected pressure and temperature, such as 420 psia and 300K. The high pressure primary gas mixture then flows from the outlet 132 of the primary compressor 130, through a first primary heat exchanger 140, which can be a miniature heat exchanger located in the handle of a cryoprobe. Specifically, the high pressure primary gas mixture passes through the high pressure passageway 142 of the first primary heat exchanger 140, where it is cooled to a lower temperature, such as for example 280K. Depending upon the required temperatures and cooling power, some applications may not require the first primary heat exchanger 140.

The high pressure gas mixture then passes through a primary/secondary heat exchanger 240, specifically through the high pressure primary passageway 170 of the primary/secondary heat exchanger 240, where it is further cooled to a lower temperature such as 220K. The high pressure primary gas mixture then passes through a second primary heat exchanger 160, specifically through the high pressure passageway 162, where it is still further cooled to, for example, 160K. This second primary heat exchanger can be comparable to the laminated heat exchangers discussed above in the non-precooled systems. Depending upon the required temperatures and cooling power, some applications may not require the second primary heat exchanger 160.

The gas mixture then flows to the primary Joule-Thomson expansion element 150. After isenthalpic expansion in the primary expansion element 150, to a temperature such as 130K, the expanded low pressure gas mixture cools the target tissue T.

Then, the low pressure primary gas mixture passes back through a low pressure passageway 164 in the second primary heat exchanger 160, where it is warmed to 220K, and through a low pressure passageway 144 in the first primary heat exchanger 140, where it is warmed to 300K. The low pressure gas mixture then returns to the inlet 134 of the primary compressor 130.

The secondary loop 200 consists of a high pressure path 210 and a low pressure path 220. A secondary loop compressor 230 compresses the secondary refrigerant to a pressure which can be relatively higher than the pressure found in the primary system, since the secondary system does not enter the cannula of the probe. The high pressure secondary refrigerant then flows from the outlet 232 of the secondary compressor 230, through a primary/secondary heat exchanger 240, which can also be a miniature heat exchanger located in the handle of the cryoprobe. Specifically, the high pressure secondary refrigerant passes through the secondary high pressure passageway 242 of the primary/secondary heat exchanger 240, where it is cooled to a lower temperature.

The high pressure secondary refrigerant then passes through a secondary Joule-Thomson expansion element 250.

After isenthalpic expansion in the secondary expansion element 250, the expanded low pressure secondary refrigerant passes back through a low pressure passageway 244 in the primary/secondary heat exchanger 240. The low pressure passageway 244 is situated so as to insulate the high pressure primary passageway 170 from the high pressure secondary passageway 242. This insures that heat flows from the high pressure passageways to the low pressure passageway. The low pressure secondary refrigerant then returns to the inlet 234 of the secondary compressor 230.

Figure 34:
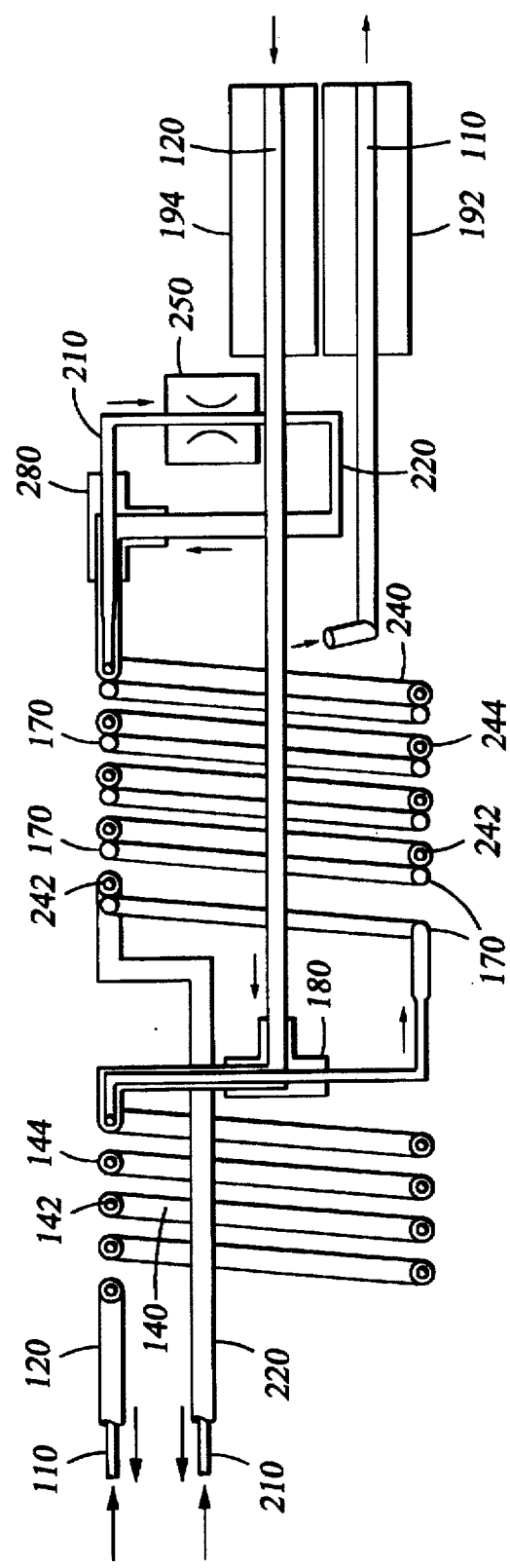
FIG. 34 is a section view of the portion of the primary closed loop and the secondary closed loop of the present invention, as they could be arranged in the handle of a cryoprobe.
Figures 36, 37:
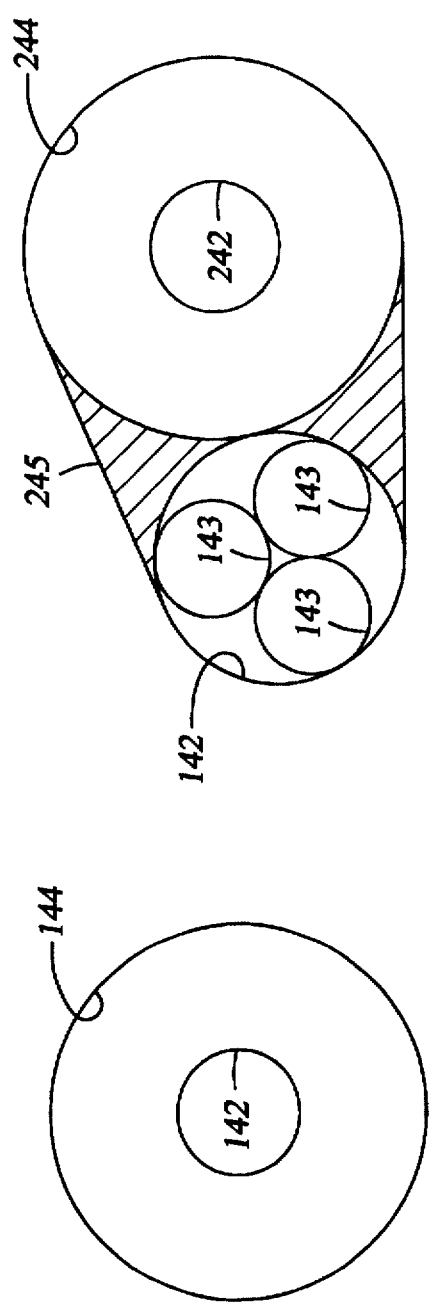
FIG. 36 is a transverse section view of the coaxial dual lumen tube used in the miniature primary heat exchanger located in the handle of the cryoprobe.
FIG. 37 is a transverse section view of the coiled multiple lumen tubes used in the primary/secondary heat exchanger.

FIG. 34 shows the portion of the dual loop refrigeration system that might be located in the handle of a cryoprobe. The primary loop 100 enters the handle as a coaxial dual lumen tube, with the high pressure path 110 being in the inner lumen, and the low pressure path 120 being in the outer lumen. The first primary heat exchanger 140 is also constructed as a coaxial coiled tube, with the high pressure passageway 142 being in the inner lumen, and the low pressure passageway 144 being in the outer lumen. The details of the dual lumen coaxial tube are shown in FIG. 36. Both the high and low pressure paths 110, 120 pass into a first splitting tee fitting 180. In the splitting tee fitting 180, the high pressure path 110 is split from the low pressure path 120. From the first tee fitting 180, the high pressure path 110 passes to the high pressure primary passageway 170 in the primary/secondary heat exchanger 240.

The primary/secondary heat exchanger 240 is constructed as a coiled multi-lumen tube, as shown in FIG. 37. The high and low pressure paths 210, 220 pass through a dual lumen coaxial tube. The high pressure secondary path 210 passes through the inner lumen, high pressure secondary passageway 242, and the low pressure secondary path 220 passes through the outer lumen, low pressure secondary passageway 244. Soldered to the outside of the low pressure secondary passageway 244 is the high pressure primary passageway 142. The high pressure primary passageway 142 can have a plurality of inner lumens 143, with the high pressure primary gas mixture flowing through all of the inner lumens 143, and through the interstitial spaces between and around the inner lumens 143. This arrangement promotes improved heat transfer to the solder and to the low pressure secondary passageway 244.

After exiting the primary/secondary heat exchanger 240, the high pressure primary path 110 flows through a high pressure primary connector 192, which can be connected to the cannula of the cryoprobe, and to the primary expansion element 150 in the cold tip. After expansion in the expansion element 150, the low pressure gas mixture flows back through a low pressure primary connector 194 to the tee fitting 180. In the tee fitting 180, the low pressure primary passageway 144 rejoins the high pressure primary passageway 142 in a coaxial relationship to return to the primary compressor 130.

The secondary loop 200 also enters the cryoprobe handle, coming from the secondary compressor 230, as a coaxial dual lumen tube, with the high pressure path 210 being in the inner lumen, and the low pressure path 220 being in the outer lumen. The secondary high and low pressure paths 210, 220 pass through the primary/secondary heat exchanger 240 as described above, and connect to a second splitting tee fitting 280. In the second tee fitting 280, the high pressure secondary path 210 splits from the low pressure secondary path 220 and passes through the secondary expansion element 250. After expansion in the secondary expansion element 250, the low pressure secondary refrigerant passes into the low pressure secondary path 220, which rejoins the high pressure secondary path 210 in the second tee fitting 280.

Figure 35:
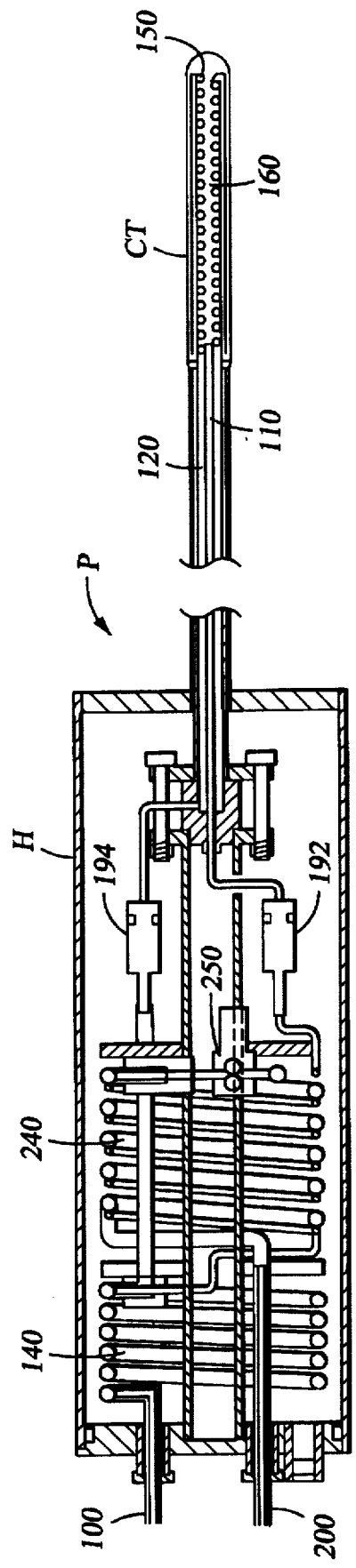
FIG. 35 is a section view of a hand held cryoprobe according to the present invention.

FIG. 35 shows how the apparatus of the present invention might be arranged in a rigid cryoprobe P, having a handle H. The primary and secondary closed loop systems 100, 200 enter the end of the handle H. The primary gas mixture passes through the first primary heat exchanger 140, while the first primary heat exchanger 140 is bypassed by the secondary refrigerant. Both the primary gas mixture and the secondary refrigerant pass through the primary/secondary heat exchanger 240 as described earlier. The secondary refrigerant is then isenthalpically expanded in the secondary expansion element 250 and returns through the primary/secondary heat exchanger 240. The secondary refrigerant then exits the handle H to return to the secondary compressor 230. The primary gas mixture passes through the connectors 192, 194 to the cold tip CT. In the cold tip CT, the high pressure primary gas mixture passes through the microminiature primary heat exchanger 160, and then through the primary expansion element 150. The microminiature heat exchanger 160 is shown as a coiled high pressure tube, with the low pressure primary gas mixture returning through the coils. Having expanded and cooled, the low pressure primary gas mixture flows back through the microminiature primary heat exchanger 160, and the first primary heat exchanger 140, before exiting the handle H to return to the primary compressor 130.

While the particular invention as herein shown and disclosed in detail is fully capable of fulfilling the objects previously stated, it is to be understood that this disclosure is merely an illustration of the presently preferred embodiments of the invention and that no limitations are intended other than those described in the appended claims.

We claim:

1. A method for cooling a distal cold tip of a probe, comprising:

providing a closed primary loop, said primary loop including at least one primary heat exchanger and
a primary expansion element distal of said primary heat exchanger;

providing a closed secondary loop, said secondary loop including a primary/secondary heat exchanger
and a secondary expansion element distal of said primary/secondary heat exchanger;

compressing a refrigerant in said secondary loop;

cooling said refrigerant in said primary/secondary heat exchanger;

isenthalpically expanding said refrigerant to a lower temperature with said secondary expansion element;

warming said expanded refrigerant in said primary/secondary heat exchanger;

compressing a gas mixture in said primary loop with said primary compressor;

cooling said compressed gas mixture in said primary heat exchanger;

cooling said compressed gas mixture in said primary/secondary heat exchanger;

isenthalpically expanding said gas mixture with said primary expansion element to still further cool said gas mixture;

and applying said expanded gas mixture to the cold tip, to lower the temperature of the cold tip.

2. A method as recited in claim 1, further comprising solidifying liquid contaminants of said gas mixture in said primary/secondary heat exchanger, thereby removing said contaminants from said gas mixture prior to passage of said gas mixture through said primary expansion element.

3. A method for cooling a distal cold tip of a probe, comprising:

providing a closed primary loop, said primary loop including a primary compressor, a primary heat exchanger distal of said primary compressor, and a primary expansion element distal of said primary heat exchanger;

providing a closed secondary loop, said secondary loop including a secondary compressor, a primary/secondary heat exchanger distal of said secondary compressor, and a secondary expansion element distal of said primary/secondary heat exchanger;

compressing a refrigerant in said secondary loop with said secondary compressor;

cooling said compressed refrigerant in a high pressure secondary side of said primary/secondary heat exchanger;

isenthalpically expanding said refrigerant with said secondary expansion element;

warming said expanded refrigerant in a low pressure secondary side of said primary/secondary heat exchanger;

returning said expanded refrigerant to an inlet of said secondary compressor;

compressing a gas mixture in said primary loop with said primary compressor;

cooling said compressed gas mixture in a high pressure side of said primary heat exchanger;

cooling said compressed gas mixture in a high pressure primary side of said primary/secondary heat exchanger;

isenthalpically expanding said gas mixture with said primary expansion element to still further cool said gas mixture;

applying said expanded gas mixture to the cold tip, to lower the temperature of the cold tip;

warming said expanded gas mixture in a low pressure side of said primary heat exchanger; and returning said expanded gas mixture to an inlet of said primary compressor.

4. A method as recited in claim 3, further comprising solidifying liquid contaminants of said gas mixture in restrictions in said high pressure primary side of said primary/secondary heat exchanger, thereby removing said contaminants from said gas mixture prior to passage of said gas mixture through said primary expansion element.

5. A method as recited in claim 3, further comprising:

providing a distal primary heat exchanger between said primary/secondary heat exchanger and said primary expansion element;

still further cooling said compressed gas mixture in a high pressure side of said distal primary heat exchanger; and warming said expanded gas mixture in a low pressure side of said distal primary heat exchanger prior to passage of said expanded gas mixture through said low pressure side of said first primary heat exchanger.

6. A method for cooling a cold tip of a probe, comprising:

providing a gas mixture capable of isenthalpically expanding to a temperature below 183 K from a pressure of no more than 420 psia;

providing a closed primary loop having a compressor for pressurizing said gas mixture to a pressure of no more than 420 psia, at least one primary heat exchanger, and a primary expansion element adjacent to a metallic heat transfer element in said cold tip;

providing a closed secondary loop having a compressor, a primary/secondary heat exchanger, and a secondary expansion element;

placing said heat transfer element in contact with a remote body to be cooled;

compressing a refrigerant in said secondary loop;

conducting said compressed refrigerant to a high pressure secondary section of said primary/secondary heat exchanger;

cooling said compressed refrigerant in said high pressure secondary section of said primary/secondary heat exchanger;

isenthalpically expanding said refrigerant in said secondary expansion element;

conducting said expanded refrigerant to a low pressure secondary section of said primary/secondary heat exchanger;

warming said expanded refrigerant in said low pressure secondary section of said primary/secondary heat exchanger;

compressing said gas mixture to no more than 420 psia;

conducting said compressed gas mixture to a high pressure section of said primary heat exchanger;

cooling said compressed gas mixture in said high pressure section of said primary heat exchanger;

conducting said compressed gas mixture to a high pressure primary section of said primary/secondary heat exchanger;

cooling said compressed gas mixture in said high pressure primary section of said primary/secondary heat exchanger;

isenthalpically expanding said gas mixture in said primary expansion element to still further cool said gas mixture to below 183 K;

absorbing heat from said heat transfer element by contact with said expanded gas mixture, to cool said heat transfer element to below 180 K; and absorbing heat from said body to be cooled, by contact with said heat transfer element.

7. A method as recited in claim 6, further comprising solidifying liquid contaminants of said gas mixture in restrictions in said high pressure primary section of said primary/secondary heat exchanger, thereby removing said contaminants from said gas mixture prior to passage of said gas mixture through said primary expansion element.

8. A method as recited in claim 6, further comprising:

providing a distal primary heat exchanger between said primary/secondary heat exchanger and said primary expansion element;

still further cooling said compressed gas mixture in a high pressure side of said distal primary heat exchanger; and warming said expanded gas mixture in a low pressure side of said distal primary heat exchanger prior to passage of said expanded gas mixture through said low pressure side of said first primary heat exchanger.

9. A miniature mixed gas refrigeration system, comprising:

a closed primary loop for circulating a gas mixture, with a high pressure primary flow path and a low pressure primary flow path, said primary loop including a primary compressor, and a primary expansion element for isenthalpically expanding said gas mixture from said high pressure primary flow path to said low pressure primary flow path; and a closed secondary loop for circulating a refrigerant, with a high pressure secondary flow path and a low pressure secondary flow path, said secondary loop including a secondary compressor, a primary/secondary heat exchanger, and a secondary expansion element for isenthalpically expanding said refrigerant from said high pressure secondary flow path downstream of said primary/secondary heat exchanger to said low pressure secondary flow path upstream of said primary/secondary heat exchanger;

wherein said high pressure primary flow path, said high pressure secondary flow path, and said low pressure secondary flow path pass through said primary/secondary heat exchanger in a heat exchange relationship; and wherein said low pressure primary flow path bypasses said primary/secondary heat exchanger.

10. A miniature mixed gas refrigeration system as recited in claim 9, further comprising a primary heat exchanger, having high pressure and low pressure primary flow paths, between said primary compressor and said primary/secondary heat exchanger.

11. A miniature mixed gas refrigeration system as recited in claim 10, wherein said primary heat exchanger comprises a coaxial dual lumen coiled tube, with said high pressure primary flow path connected to an inner said lumen and said low pressure primary flow path connected to an outer said lumen.

12. A miniature mixed gas refrigeration system as recited in claim 9, further comprising a primary heat exchanger, having high pressure and low pressure primary flow paths, between said primary/secondary heat exchanger and said primary expansion element.

13. A miniature mixed gas refrigeration system as recited in claim 9, wherein said primary high pressure flow path in said primary/secondary heat exchanger is insulated from said secondary high pressure flow path by said secondary low pressure flow path.

14. A miniature mixed gas refrigeration system as recited in claim 13, wherein:

said secondary high and low pressure flow paths in said primary/secondary heat exchanger are formed as a first tube having two coaxial lumens, with an inner said lumen forming said secondary high pressure flow path and an outer said lumen forming said secondary low pressure flow path; and said primary high pressure flow path in said primary/secondary heat exchanger comprises a second tube mounted to an outer wall of said first tube in a parallel arrangement.

15. A miniature mixed gas refrigeration system, comprising:

a closed primary loop for circulating a gas mixture, with a high pressure primary flow path and a low pressure primary flow path, said primary loop including a primary compressor, a primary heat exchanger with high pressure and low pressure primary flow paths, a primary expansion element for isenthalpically expanding said gas mixture from said high pressure primary flow path downstream of said primary heat exchanger to said low pressure primary flow path upstream of said primary heat exchanger; and a closed secondary loop for circulating a refrigerant, with a high pressure secondary flow path and a low pressure secondary flow path, said secondary loop including a secondary compressor, a primary/secondary heat exchanger, and a secondary expansion element for isenthalpically expanding said refrigerant from said high pressure secondary flow path downstream of said primary/secondary heat exchanger to said low pressure secondary flow path upstream of said primary/secondary heat exchanger;

wherein said high pressure primary flow path, said high pressure secondary flow path, and said low pressure secondary flow path pass through said primary/secondary heat exchanger in a heat exchange relationship; and wherein said low pressure primary flow path bypasses said primary/secondary heat exchanger.

16. A miniature mixed gas refrigeration system as recited in claim 15, further comprising a second primary heat exchanger having high pressure and low pressure primary flow paths between said first primary heat exchanger and said primary expansion element.

17. A miniature mixed gas refrigeration system as recited in claim 15, wherein said primary heat exchanger comprises a coaxial dual lumen coiled tube, with said high pressure primary flow path connected to an inner said lumen and said low pressure primary flow path connected to an outer said lumen.

18. A miniature mixed gas refrigeration system as recited in claim 15, wherein said primary high pressure flow path in said primary/secondary heat exchanger is insulated from said secondary high pressure flow path by said secondary low pressure flow path.

19. A miniature mixed gas refrigeration system as recited in claim 18, wherein:

said secondary high and low pressure flow paths in said primary/secondary heat exchanger are formed as a first tube having two coaxial lumens, with an inner said lumen forming said secondary high pressure flow path and an outer said lumen forming said secondary low pressure flow path; and said primary high pressure flow path in said primary/secondary heat exchanger comprises a second tube mounted to an outer wall of said first tube in a parallel arrangement.

20. A miniature mixed gas refrigeration system, comprising:

a probe having a proximal handle and a distal cold tip;

a closed primary loop for circulating a gas mixture, said primary loop including:

a primary compressor connected to said probe;

a miniature primary expansion element adjacent said cold tip for isenthalpically expanding said gas mixture from a high pressure flow path of said primary loop to a low pressure flow path of said primary loop; and a primary heat exchanger in said handle, said primary heat exchanger having high pressure and low pressure primary flow paths;

a heat transfer body in said cold tip, said heat transfer body having an inner surface exposed to said expanded gas mixture and an outer surface exposed to ambient, for transferring heat from ambient to said gas mixture; and a closed secondary loop for circulating a refrigerant, said secondary loop including:

a secondary compressor connected to said probe;

a secondary expansion element in said handle for isenthalpically expanding said refrigerant from a high pressure flow path of said secondary loop to a low pressure flow path of said secondary loop; and a primary/secondary heat exchanger in said handle, said primary/secondary heat exchanger having a high pressure primary flow path, a high pressure secondary flow path, and a low pressure secondary flow path;

wherein said low pressure primary flow path bypasses said primary/secondary heat exchanger.

21. A miniature mixed gas refrigeration system as recited in claim 20, further comprising a second primary heat exchanger adjacent said cold tip, said second primary heat exchanger having high pressure and low pressure primary flow paths between said first primary heat exchanger and said primary expansion element.

22. A miniature mixed gas refrigeration system as recited in claim 20, wherein said primary heat exchanger comprises a dual lumen tube, with said high pressure flow path comprising a first said lumen and said low pressure flow path comprising a second said lumen.

23. A miniature mixed gas refrigeration system as recited in claim 22, wherein said first and second lumens are coaxial.

24. A miniature mixed gas refrigeration system as recited in claim 23, wherein said dual lumen coaxial tube forms a coil.

25. A miniature mixed gas refrigeration system as recited in claim 20, wherein said primary high pressure path in said primary/secondary heat exchanger is insulated from said secondary high pressure path by said secondary low pressure path.

26. A miniature mixed gas refrigeration system as recited in claim 25, wherein:

said secondary high and low pressure paths in said primary/secondary heat exchanger are formed as a first tube having two coaxial lumens, with an inner said lumen forming said secondary high pressure path and an outer said lumen forming said secondary low pressure path; and said primary high pressure path in said primary/secondary heat exchanger comprises a second tube mounted to an outer wall of said first tube in a parallel arrangement.

27. A miniature mixed gas refrigeration system as recited in claim 20, wherein a high pressure portion of said primary loop comprises a tube having a plurality of high pressure lumens.

28. A miniature mixed gas refrigeration system as recited in claim 27, wherein said tube comprises:

an outer lumen; and a plurality of inner lumens within said outer lumen, each said lumen having a wall in contact with a wall of at least one other said lumen.

29. A miniature mixed gas refrigeration system as recited in claim 28, wherein each said inner lumen has a wall in contact with a wall of at least one other said inner lumen and a wall in contact with a wall of said outer lumen.

30. A miniature mixed gas refrigeration system, comprising:

a primary loop compressor for pressurizing a gas mixture to a pressure of approximately 420 psia, said primary compressor having an inlet and an outlet;

a dual lumen primary loop tube, said primary loop tube having a high pressure lumen connected to an outlet of said primary compressor and a low pressure lumen connected to an inlet of said primary compressor;

a primary loop heat exchanger attached to said primary loop tube, said primary loop heat exchanger having a high pressure passageway connected to said high pressure lumen and a low pressure passageway connected to said low pressure lumen;

a primary loop expansion element connected to said high pressure passageway of said primary loop heat exchanger for isenthalpically expanding said gas mixture from said higher pressure to a lower pressure, said expanded gas mixture thereby cooling to a temperature of no greater than 183 K, said expanded gas mixture being in fluid flow communication with said low pressure passageway;

a secondary loop compressor for compressing a refrigerant, said secondary compressor having an inlet and an outlet;

a dual lumen secondary loop tube, said secondary loop tube having a high pressure lumen connected to an outlet of said secondary compressor and a low pressure lumen connected to an inlet of said secondary compressor;

a primary/secondary heat exchanger attached to a distal end of said secondary loop tube, said primary/secondary heat exchanger having a primary loop high pressure passageway connected to said primary loop high pressure lumen, a secondary loop high pressure passageway connected to said secondary loop high pressure lumen, and a secondary loop low pressure passageway connected to said secondary loop low pressure lumen; and a secondary loop expansion element connected to said secondary loop high pressure passageway of said primary/secondary heat exchanger for isenthalpically expanding said refrigerant, said expanded gas mixture being in fluid flow communication with said secondary loop low pressure passageways;

wherein said low pressure primary flow path bypasses said primary/secondary heat exchanger.

31. A miniature mixed gas refrigeration system as recited in claim 30, further comprising a cold tip primary loop heat exchanger, said cold tip primary loop heat exchanger having a high pressure passageway connected to said high pressure lumen of said primary loop tube between said primary/secondary heat exchanger and said primary loop expansion element, and said cold tip primary loop heat exchanger having a low pressure passageway connected to said low pressure lumen of said primary loop tube between said first primary loop heat exchanger and said primary loop expansion element.

32. A miniature mixed gas refrigeration system as recited in claim 30, wherein said primary loop heat exchanger comprises a dual lumen coaxial tube, with said high pressure passageway comprising a first said lumen and said low pressure passageway comprising a second said lumen.

33. A miniature mixed gas refrigeration system as recited in claim 32, wherein said dual lumen coaxial tube forms a coil.

34. A miniature mixed gas refrigeration system as recited in claim 30, wherein said primary loop high pressure passageway is insulated from said secondary loop high pressure passageway by said secondary loop low pressure passageway.

35. A miniature mixed gas refrigeration system as recited in claim 34, wherein:

said secondary loop high and low pressure passageways are formed as a first tube having two coaxial lumens, with an inner said lumen forming said secondary loop high pressure passageway and an outer said lumen forming said secondary loop low pressure passageway; and said primary loop high pressure passageway comprises a second tube mounted to an outer wall of said first tube in a parallel arrangement.

36. A miniature mixed gas refrigeration system as recited in claim 35, wherein said second tube comprises:

an outer lumen; and a plurality of inner lumens within said outer lumen, each said lumen having a wall in contact with a wall of at least one other said lumen.

* * * * *

(12) REEXAMINATION CERTIFICATE (4474th)
United States Patent
Dobak, III et al.

(10) Number: US 5,758,505 C1
(45) Certificate Issued: Oct. 30, 2001

(54) PRECOOLING SYSTEM FOR JOULE-THOMSON PROBE

(75) Inventors: John D. Dobak, III; Terry L. Brown; Kambiz Ghaerzadeh; Xiaoyu Yu, all of San Diego, CA (US)

(73) Assignee: Cryogen, Inc., San Diego, CA (US)

Reexamination Requests:
No. 90/005,697, Apr. 5, 2000
No. 90/005,901, Jan. 3, 2001

Reexamination Certificate for:
Patent No.: 5,758,505
Issued: Jun. 2, 1998
Appl. No.: 08/726,770
Filed: Oct. 7, 1996

Related U.S. Application Data

(63) Continuation-in-part of application No. 08/698,044, filed on Aug. 15, 1996, which is a continuation-in-part of application No. 08/542,123, filed on Oct. 12, 1995.

(51) Int. Cl.$^7$ .............................. F25B 19/02; F25B 9/00
(52) U.S. Cl. .............................. 62/6; 62/51.2; 62/293; 606/23
(58) Field of Search .................................................. 62/6

(56) References Cited

U.S. PATENT DOCUMENTS

| | | |
|---|---|---|
| 2,319,542 | 5/1943 | Hall . |
| 2,672,032 | 3/1954 | Towse . |
| 3,272,203 | 9/1966 | Chato . |

(List continued on next page.)

FOREIGN PATENT DOCUMENTS

| | | |
|---|---|---|
| 0271989 | 6/1988 | (EP) . |
| 1465540 | 1/1967 | (FR). |

(List continued on next page.)

OTHER PUBLICATIONS

*CryoGen's Brief in Support of the Construction of Claims 1, 3, & 6 of U.S. Pat. No. 5,758,505 for "Precooling System for Joule–Thomson Probe"*, FemRx, Inc. v. CryoGen, Inc., Case No. C98–02330 VRW (N.D. Cal. filed Jun. 8, 1998); CryoGen, Inc. v. Johnson & Johnson, Inc., Case No. C99–02471 VRW (N.D. Cal. filed May 25, 1999) (consolidated).

(List continued on next page.)

Primary Examiner—William C Doerrler

(57) ABSTRACT

A miniature mixed gas refrigeration system and method of operation are disclosed. An optimum gas mixture is formulated from a group of component fluids, according to calculated thermodynamic properties of a group of candidate fluid mixtures. The gas mixture is pressurized by a compressor to a pressure less than 420 psia, for safety reasons. The compressed gas mixture is passed through a primary heat exchanger, and then through a primary-to-secondary heat exchanger, to precool the gas mixture. The secondary side of the primary/secondary heat exchanger is cooled by a secondary Joule-Thomson refrigeration system. Properly sized flow restrictions in the primary side of the primary/secondary heat exchanger can solidify and trap liquid contaminants that may be in the gas mixture. The gas mixture exiting the primary outlet of the primary/secondary heat exchanger passes to a primary Joule-Thomson expansion element where the high pressure gas is expanded isenthalpically to a lower temperature at least as low as 183K. This low temperature gas cools a heat transfer element mounted in the outer wall of the catheter, to cool an external object. Return gas flows back through the primary heat exchanger to further pre-cool the incoming high pressure gas mixture. A distal primary heat exchanger can be added between the primary/secondary heat exchanger and the primary Joule-Thomson expansion element.

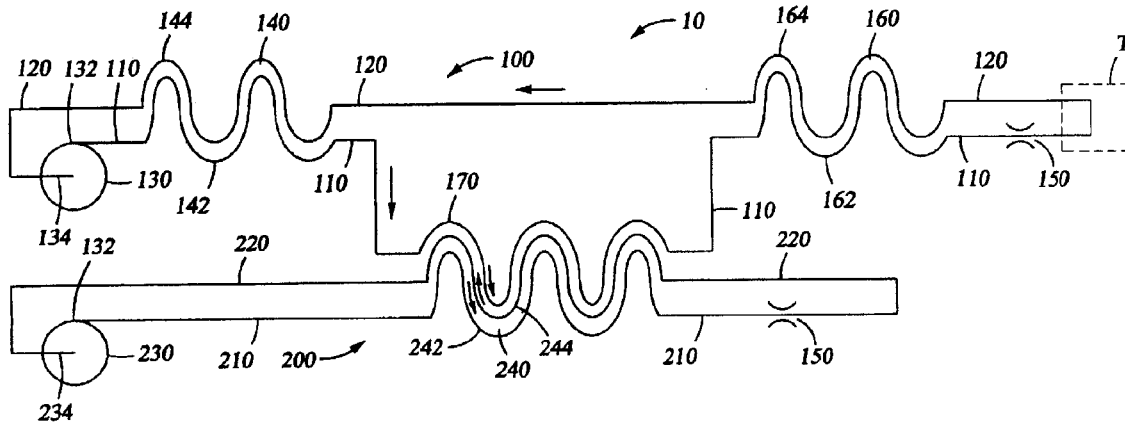

U.S. PATENT DOCUMENTS

| | | |
|---|---|---|
| 3,273,356 | 9/1966 | Hoffman . |
| 3,298,371 | 1/1967 | Lee . |
| 3,398,738 | 8/1968 | Lamb et al. . |
| 3,401,533 | 9/1968 | Maybury . |
| 3,431,750 | 3/1969 | Lefranc . |
| 3,439,680 | 4/1969 | Thomas . |
| 3,477,434 | 11/1969 | Hood et al. . |
| 3,536,075 | 10/1970 | Thomas et al. . |
| 3,613,689 | 10/1971 | Crump . |
| 3,630,203 | 12/1971 | Sellinger et al. . |
| 3,662,755 | 5/1972 | Rautenbach et al. . |
| 3,729,945 | 5/1973 | Linnett . |
| 3,750,417 | 8/1973 | Johannes et al. . |
| 3,768,273 | 10/1973 | Missimer . |
| 3,827,436 | 8/1974 | Stumpf et al. . |
| 3,889,680 | 6/1975 | Armao . |
| 3,913,581 | 10/1975 | Ritson et al. . |
| 3,924,628 | 12/1975 | Droegemueller et al. . |
| 3,932,154 | 1/1976 | Coers et al. . |
| 3,971,383 | 7/1976 | van Gerven . |
| 4,015,606 | 4/1977 | Mitchiner et al. . |
| 4,206,609 | 6/1980 | Durenec . |
| 4,207,897 | 6/1980 | Lloyd et al. . |
| 4,275,734 | 6/1981 | Mitchiner . |
| 4,377,168 | 3/1983 | Rzasa . |
| 4,601,296 | 7/1986 | Yerushalmi . |
| 4,781,033 | 11/1988 | Steyert et al. . |
| 4,829,785 | 5/1989 | Hersey . |
| 4,840,043 | 6/1989 | Sakitani . |
| 4,875,346 | 10/1989 | Jones et al. . |
| 4,990,412 | 2/1991 | Hersey . |
| 5,063,747 | 11/1991 | Jones et al. . |
| 5,077,979 | 1/1992 | Skertic et al. . |
| 5,078,713 | 1/1992 | Varney . |
| 5,101,894 | 4/1992 | Hendricks . |
| 5,139,496 | 8/1992 | Hed . |
| 5,147,355 | 9/1992 | Friedman et al. . |
| 5,150,579 | 9/1992 | Hingst . |
| 5,157,938 | 10/1992 | Bard et al. . |
| 5,193,349 | 3/1993 | Laverman et al. . |
| 5,275,595 | 1/1994 | Dobak, III . |
| 5,281,213 | 1/1994 | Milder et al. . |
| 5,281,215 | 1/1994 | Milder . |
| 5,281,217 | 1/1994 | Edwards et al. . |
| 5,324,286 | 6/1994 | Fowle . |
| 5,334,181 | 8/1994 | Rubinsky et al. . |
| 5,337,572 | 8/1994 | Longsworth . |
| 5,365,750 | 11/1994 | Greenthal . |
| 5,423,807 | 6/1995 | Milder . |
| 5,522,870 | 6/1996 | Ben-Zion . |
| 5,573,532 | 11/1996 | Chang et al. . |
| 5,595,065 | 1/1997 | Boiarski et al. . |
| 5,617,739 | 4/1997 | Little . |
| 5,644,502 | 7/1997 | Little . |
| 5,674,218 | 10/1997 | Rubinsky et al. . |
| 5,724,832 | 3/1998 | Little et al. . |

FOREIGN PATENT DOCUMENTS

| | | |
|---|---|---|
| 1468862 | 2/1967 | (FR) . |
| 2 482 445 | 3/1980 | (FR) . |
| 2477406 | 9/1981 | (FR) . |
| 1336892 | 11/1973 | (GB) . |
| 2 026 324 | 2/1980 | (GB) . |
| 2080117 | 2/1982 | (GB) . |
| 2 093 964 | 9/1982 | (GB) . |
| 2 283 678 | 5/1995 | (GB) . |
| 2 289 412 | 11/1995 | (GB) . |
| 2 289 413 | 11/1995 | (GB) . |
| 2 289 414 | 11/1995 | (GB) . |
| 2 289 510 | 11/1995 | (GB) . |
| 57-126430 | 8/1982 | (JP) . |
| 333857 | 4/1974 | (SU) . |
| 333858 | 4/1974 | (SU) . |
| 527467 | 9/1976 | (SU) . |
| 534484 | 11/1976 | (SU) . |
| 565052 | 7/1977 | (SU) . |
| 573496 | 9/1977 | (SU) . |
| 627154 | 10/1978 | (SU) . |
| 637417 | 12/1978 | (SU) . |
| 676604 | 7/1979 | (SU) . |
| 907054 | 7/1980 | (SU) . |
| 768795 | 10/1980 | (SU) . |
| 802348 | 2/1981 | (SU) . |
| 802349 | 2/1981 | (SU) . |
| 802350 | 2/1981 | (SU) . |
| 802351 | 2/1981 | (SU) . |
| 832268 | 5/1981 | (SU) . |
| 839516 | 6/1981 | (SU) . |
| 918298 | 4/1982 | (SU) . |
| 966107 | 10/1982 | (SU) . |
| 1026795 | 7/1983 | (SU) . |
| 1026796 | 7/1983 | (SU) . |
| 1054400 | 11/1983 | (SU) . |
| 1089099 | 4/1984 | (SU) . |
| 1090699 | 5/1984 | (SU) . |
| 1134856 | 1/1985 | (SU) . |
| 1158567 | 5/1985 | (SU) . |
| 1189434 | 11/1985 | (SU) . |
| 1437012 | 11/1988 | (SU) . |
| 1774140 | 11/1992 | (SU) . |
| WO 93/04647 | 3/1993 | (WO) . |
| WO 93/08753 | 5/1993 | (WO) . |
| 95/13025 | 5/1995 | (WO) . |
| WO 95/30379 | 11/1995 | (WO) . |
| WO 95/30380 | 11/1995 | (WO) . |

OTHER PUBLICATIONS

*Declaration of Nicolas S. Gikkas in Support of CryoGen's Brief Supporting the Construction of Claims 1, 3, & 6 of U.S. Pat. No. 5,758,505 for "Precooling System for Joule–Thomson Probe",* FemRx, Inc. v. CryoGen, Inc., Case No. C98–02330 VRW (N.D. Cal. filed Jun. 8, 1998); CryoGen, Inc. v. Johnson & Johnson, Inc., Case No. C99–02471 VRW (N.D. Cal. filed May 25, 1999) (consolidated).

*Ethicon, Inc.'s Claim Construction Brief for U.S. Pat. No. 5,758,505,* FemRx, Inc. v. CryoGen, Inc., Case No. C98–02330 VRW (N.D. Cal. filed Jun. 8, 1998); CryoGen, Inc. v. Johnson & Johnson, Inc., Case No. C99–02471 VRW (N.D. Cal. filed May 25, 1999) (consolidated).

*Declaration of John A. Barclay, Ph.D. in Support of Ethicon's Claim Construction Brief Regarding U.S. Pat. No. 5,758,505,* FemRx, Inc. v. CryoGen, Inc., Case No. C98–02330 VRW (N.D. Cal. filed Jun. 8, 1998); CryoGen, Inc. v. Johnson & Johnson, Inc., Case No. C99–02471 VRW (N.D. Cal. filed May 25, 1999) (consolidated).

*Declaration of Ernest G. Cravalho, Ph.D. in Support of Ethicon's Claim Construction Brief Regarding U.S. Pat. No. 5,758,505,* FemRx, Inc. v. CryoGen, Inc., Case No. C98–02330 VRW (N.D. Cal. filed Jun. 8, 1998); CryoGen, Inc. v. Johnson & Johnson, Inc., Case No. C99–02471 VRW (N.D. Cal. filed May 25, 1999) (consolidated).

*Declaration of Peter J. Curtin in Support of Ethicon, Inc.'s Claim Construction Brief for U.S. Pat. No. 5,758,505,* FemRx, Inc. v. CryoGen, Inc., Case No. C98–02330 VRW (N.D. Cal. filed Jun. 8, 1998); CryoGen, Inc. v. Johnson & Johnson, Inc., Case No. C99–02471 VRW (N.D. Cal. filed May 25, 1999) (consolidated).

*CryoGen's Reply Brief in Support of the Construction of Claims 1, 3, & 6 of U.S. Pat. No. 5,758,505 for "Precooling System for Joule–Thomson Probe"*, FemRx, Inc. v. CryoGen, Inc., Case No. C98–02330 VRW (N.D. Cal. filed Jun. 8, 1998); CryoGen, Inc. v. Johnson & Johnson, Inc., Case No. C99–02471 VRW (N.D. Cal. filed May 25, 1999) (consolidated).

*Duane Everett Townsend, M.D. F.A.C.O.G.'s Declaration in Support of CryoGen's Construction of Claims 1, 3, & 6 of U.S. Pat. No. 5,758,505 for "Precooling System for Joule–Thomson Probe"*, FemRx, Inc. v. CryoGen, Inc., Case No. C98–02330 VRW (N.D. Cal. filed Jun. 8, 1998); CryoGen, Inc. v. Johnson & Johnson, Inc., Case No. C99–02471 VRW (N.D. Cal. filed May 25, 1999) (consolidated).

*Dr. Graham Walker's Declaration in Support of CryoGen's Construction of Claims 1, 3, & 6 of U.S. Pat. No. 5,758,505 for "Precooling System for Joule–Thomson Probe"*, FemRx, Inc. v. CryoGen, Inc., Case No. C98–02330 VRW (N.D. Cal. filed Jun. 8, 1998); CryoGen, Inc. v. Johnson & Johnson, Inc., Case No. C99–02471 VRW (N.D. Cal. filed May 25, 1999) (consolidated).

*Declaration of Nicolas S. Gikkas in Support of CryoGen's Reply Brief in Support of the Construction of Claims 1, 3, & 6 of U.S. Pat. No. 5,758,505 for "Precooling System for Joule–Thomson Probe"*, FemRx, Inc. v. CryoGen, Inc., Case No. C98–02330 VRW (N.D. Cal. filed Jun. 8, 1998); CryoGen, Inc. v. Johnson & Johnson, Inc., Case No. C99–02471 VRW (N.D. Cal. filed May 25, 1999) (consolidated).

Amoils, S.P., The Joule–Thomson Cryoprobe, 78 Arch. Ophthal. 201–207 (Aug. 1967).

Bard, S. et al., A Two–Stage 80 K/140 K Sorption Cryocooler, Proceeding of the 12$^{th}$ International Cryogenic Engineering Conference 626–630 (R.G. Scurlock & C.A. Bailey, eds.) (Butterworth, Guilford, UK 1988).

Baust, J. et al., Underlying Mechanisms of Damage and New Concepts in Cryosurgical Instrumentation, *Cryosurgery: Mechanisms and Applications*, 21–36 (International Institute of Refrigeration, Paris 1995).

Bodio, E., *Application of Multicomponent Gaseous Mixtures in Linde–Hampson Coolers*, WROCLAW Inst. of Tech. (1985).

Brodjanskij, V.M., Development of Low–Temperature Engineering Until 2000, OEDB, 90:048732, 25:4 Luft–und Kaeltetechnik (German Democratic Republic) 193–195 (1989).

Chang, Z. et al., Development of a High–Performance Multiprobe Cryosurgical Device, 28 Biomedical Instrumentation and Technology 383–390 (Sep. 1994).

Chang, Z. et al., Optimization of Cryosurgical Instrumentation for Use in Minimally Invasive Prostate Surgery, 267 Recent Advances in Cryogenic Engineering 45–55 (ASME 1993).

Cryogen Documents, Bates No. CRY 000428–CRY 000479.

Droegemueller, W. et al. Cryocoagulation of the Edometrium at the Uterine Cornua, 131:1, American Journal of Obstetrics and Gynecology 1–9 (1978).

Friend, D. et al., Thermophysical Property Computer Packages from NIST, 225 ASME HTD 13–18 (1992).

Gage, A. et al., Cryosurgery, *Encyclopedia of Medical Devices and Instrumentation, vol. 2*, 893–908 (Webster, J. Ed.) (Wiley & Sons, New York 1988).

Gage, A., Current Progress in Cryosurgery, Cryobiology 25, 483–86 (Mar. 1988).

Garamy, G. Engineering Aspects of Cryosurgical Instruments Employing Liquid Nitrogen, 7 Cryosurgery 283–308 (Summer 1967).

Gassanov, L.G. et al., Experience in the Development and Operation of a Cryosurgical Apparatus, Elektronnaya Promyslennost 41–42 (No. 1, Jan.–Feb. 1987).

Grokholskii et al., The 'Krioelektronika–1' Cryogenic Dental Unit, Medicinskaya Tekhnika (Medical Technology) No. 3 at 16–20 (A.A. Bogomolets Kieve Medical Institute, May–Jun. 1982).

Hill, D., *Throttle Cycle Cooler Vibration Characterization*.

Hubbell, R., New Heat Transfer and Friction Factor Design Data for Perforated Plate Heat Exchangers, 33 Advanced Cryogenic Engineering 383–390 (1988).

Jichuan, J., Heat Transfer Characteristics of a Perforated Plate, Part II—Heat Transfer Coefficients for the Separate Working Surfaces, 30 Cryogenics 318–322 (Sep. 1990).

Jones et al., Mixed–Gas Sorption Joule–Thompson Refrigerator, 15:5, NASA Tech Briefs 39–40 (May 1991).

Jones, J., Sorption Refrigeration Research at JPL/NASA, Sci. Tech. Froid 143–152 (International Institute of Refrigeration, Paris, France 1992).

Jones, Jack A., Cryogenic Mixed Fluid Application Study and Computer Code Development, Final Report, Jet Propoulsion Laboratory (Jun. 1989–Dec. 1991).

Khatri, A., *A Throttle Cycle Refrigerator Opening Below 77K*.

Kleemenko, A.P., One Flow Cascade Cycle (in Schemes of Natural Gas Liquefaction and Separation), 1 International Congress of Refrigeration, Copenhagen 34–39 (1959).

Kobrianski, V.L. et al., A Cryomedical Device Based on a Closed Cycle Joule–Thomson Cooling System, Elektronnaya Promyshlennost (Electronics Industry), Nos. 8–9 at 71–72 (1979).

Little, W.A., Advances in Joule–Thomson Cooling, Advances in Cryogenic Engineering, vol. 35 1305–1314 (1990).

Little, W.A. et al., Development of a Low Cost, Cryogenic Refrigeration System for Cooling of Cryoelectronics, Presented at the Electronic Industries Association Meeting, San Diego, California (Jan.31$^{st}$–Feb. 1, 1996).

Little, W.A., Handwritten Notes to Valley Laboratories, Bates Nos. M00001–M00009 (Apr. 1987).

Little W.A., Recent Developments in Joule–Thompson Cooling Gases, Coolers and Compressors, International Cryocoolers Conference (1988).

Little, W.A., Microminiature Refrigerators for Joule–Thompson Cooling of Electronic Chips and Devices, 35 Advances in Cryogenic Engineering 1325–1333 (1990).

Little, W.A., Microminiature Refrigeration, 55(5) Rev. Sci. Instrum. 661–680 (May 1984).

Porter, W. et al., Processor Performance Enhancement Using CPU Sub–Cooling, Proceedings of the Technical Conference—International Electronic Packaging Conference, 242–246 (Sep. 25–28, 1994).

Rabin, Y. et al., A Compact Cryosurgical Apparatus for Minimally Invasive Procedures, 31 Biomedical Instrumentation and Technology, 251–258 (1997).

Sood, S.K., Prediction Methods for Vapour–Liquid Equilibrium in Multi–Component Cryogenic Mixtures, Cryogenics 199–207 (Jun. 1970).

Torre, D., Alternate Cryogens for Cryosurgery, 1:2, Journal of Dermatological Surgery 56–58 (Jun. 1975).

Venkatarathnam, G. et al., Heat Transfer and Flow Friction Correlations in Perforated Plate Heat Matrix Exchangers, 30 Cryogenics, 313–17 (Sep. 1990).

Venkatarathnam, G. et al., Matrix Heat Exchangers and Their Application in Cryogenic Systems, 30 Cryogenics 907–18 (Nov. 1990).

*Answer, Affirmative Defenses, and Counterclaims of Defendant Johnson & Johnson to CryoGen's First Amended Complaint for Infringement of U.S. Pat. Nos. 5,758,505 & 5,910,104,* CryoGen, Inc. v. Johnson & Johnson, Inc., Case No. C–99–02471 VRW (N.D. Cal. Aug. 31, 1999).

*Answer, Affirmative Defenses, and Counterclaims of Defendants FemRx and Ethicon to CryoGen's First Amended Complaint for Infringement of U.S. Pat. Nos. 5,758,505 & 5,910,104,* CryoGen, Inc. v. Johnson & Johnson, Inc., Case No. C–99–02471 VRW (N.D. Cal. Jul. 1, 1999).

*Answer, Affirmative Defenses, and Counterclaims of Defendants MMR Technologies, Inc. to First Amended Complaint for Infringement of U.S. Pat. Nos. 5,758,505 & 5,910,104,* CryoGen, Inc. v. Johnson & Johnson, Inc., Case No. C–99–02471 VRW (N.D. Cal. Jul. 1, 1999).

*Supplemental Responses and Objections of FemRx, Inc., Ethicon, Inc., and Johnson & Johnson to CryoGen, Inc.'s Second Set of Interrogatories,* CryoGen, Inc. v. Johnson & Johnson, Inc., Case No. C–99–02471 VRW (N.D. Cal. Jul. 1, 1999), Case No. C–99–02471 VRW (N.D. Cal) at 4–7.

*Military & Commerical Applications for Low Cost Cryocoolers,* Electronic Industries Association Cryelectronics Division (Jan. 31 and Feb. 1, 1996), CRY005604–006036.

Deposition of Gerald W. Spinks, Esq. of Spinks ("Spinks Dep."): 57–147, 148–233, 246–275, 275–325 (submitting under M.P.E.P. § 724.02).

Docket Sheet, CryoGen, Inc. v. Johnson & Johnson, Inc., Case No. C99–02471 VRW (N.D. Cal. filed May 25, 1999) (updated Mar. 30, 2000).

Docket Sheet, RemRx, Inc. v. CryoGen, Inc., Case No. C98–02330 VRW (N.D. Cal. filed Jun. 8, 1998) (updated Mar. 30, 2000).

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–36 is confirmed.

* * * * *